US008946154B2

(12) United States Patent
Parente Dueña et al.

(10) Patent No.: US 8,946,154 B2
(45) Date of Patent: Feb. 3, 2015

(54) PEPTIDE LIGANDS OF SOMATOSTATIN RECEPTORS

(75) Inventors: Antonio Parente Dueña, Sant Just Desvern-Barcelona (ES); Berta Ponsati Obiols, Barcelona (ES); Jimena Fernández Carneado, Barcelona (ES); Marc Gómez Caminals, Barcelona (ES); Ribera Jordana I Lluch, Becelona (ES)

(73) Assignee: BCN Peptides, S.A., Sant Quinti de Mediona (ES)

( * ) Notice: Subject to any disclaimer, the term of this patent is extended or adjusted under 35 U.S.C. 154(b) by 0 days.

(21) Appl. No.: 13/319,285

(22) PCT Filed: May 6, 2010

(86) PCT No.: PCT/EP2010/056152
§ 371 (c)(1),
(2), (4) Date: Jan. 4, 2012

(87) PCT Pub. No.: WO2010/128098
PCT Pub. Date: Nov. 11, 2010

(65) Prior Publication Data
US 2012/0122781 A1  May 17, 2012

(30) Foreign Application Priority Data
May 7, 2009  (ES) .................................. 200901168

(51) Int. Cl.
| A61K 38/31 | (2006.01) |
| A61K 38/22 | (2006.01) |
| C07K 14/655 | (2006.01) |
| C07K 14/575 | (2006.01) |
| G01N 33/74 | (2006.01) |
| A61K 38/00 | (2006.01) |

(52) U.S. Cl.
CPC .............. *G01N 33/74* (2013.01); *C07K 14/655* (2013.01); *A61K 38/00* (2013.01); *G01N 2333/655* (2013.01)
USPC ............. 514/11.1; 514/7.1; 514/6.9; 514/6.8; 514/1.1; 530/311; 530/300; 530/317

(58) Field of Classification Search
CPC ..... A61K 38/005; A61K 38/00; A61K 38/04; A61K 38/10; A61K 38/12; A61K 38/22; A61K 38/31; C07K 7/64; C07K 7/00; G01N 33/74
USPC ........................................................ 514/11.1
See application file for complete search history.

(56) References Cited

U.S. PATENT DOCUMENTS 3,904,594 A * 9/1975 Guillemin et al. ............ 530/311
4,133,782 A   1/1979 Vale, Jr. et al.
4,211,693 A   7/1980 Rivier et al.
5,364,851 A   11/1994 Joran
7,541,018 B2  6/2009 Maecke et al.

FOREIGN PATENT DOCUMENTS

| EP | WO 98/01474 | * 1/1998 | .......... C07K 14/665 |
| EP | 1283216 | 2/2003 | |
| WO | 9301206 | 1/1993 | |

OTHER PUBLICATIONS

Gorges et al., Thyroid (2001) vol. 11, No. 7, 647-659.*
Yabe et al., Chem. Pharm. Bull. (1978) 26(3), 993-997.*
Neelamkavil et al., J. Med. Chem. (2005) 48, 4025-4030.*
International Search Report for PCT/EP2010/056152, Completed by the European Patent Office on Aug. 9, 2010, 4 Pages.
Berge et al. Journal of Pharmaceutical Sciences Jan. 1977, vol. 66, No. 1, 19 Pages, "Review Article, Pharmaceutical Salts."
Stewart et al. Solid Phase Peptide Synthesis Second Edition 1984, 20 Pages, "The Chemistry of Solid Phase Peptide Synthesis."
Bodanszky et al. The Practice of Peptide Synthesis Second Edition 1984, 54 Pages, "The Practice of Peptide Synthesis."
Lloyd-Williams et al. Chemical Approaches to the Synthesis of Peptides and Proteins 1997, 78 Pages, "Solid-Phase Peptide Synthesis."
Kullmann. The Journal of Biological Chemistry Issue of Sep. 10, 1980, vol. 255, No. 17, p. 8234-8238, "Proteases as Catalysts for Enzymic Syntheses of Opioid Peptides."
Lloyd-Williams et al. Tetrahedron 1993, vol. 49, No. 48, p. 11065-11133, "Tetrahedron Report No. 347, Convergent Solid-Phase Peptide Synthesis."
Greene et al. Protective Groups in Organic Synthesis third edition, 1999, "The Role of Protective Groups in Organic Synthesis.", All together 20 Pages.
Atherton et al. The Practical Approach Series 1989, All together 17 Pages, "Solid Phase peptide synthesis, a practical approach."
Matsueda et al. Peptides 1981, vol. 2, p. 45-50, "A p-Methylbenzhydrylamine Resin for Improved Solid-Phase Syntheis of Peptide Amides."
Barlos et al. Tetrahedron Letters 1989, vol. 30, No. 30, p. 3943-3946, "Darstellung Geschutzter Peptid-Fragmente Unter Einsatz Substituierter Triphenylmethyl-Harze."
Barlos et al. Tetrahedron Letters 1989, vol. 30, No. 30, p. 3947-3950, "Veresterung Von Partiell Geschutzten Peptid-Fragmenten Mit Harzen. Einsatz Von 2-Chlortritylchlorid Zur Synthese Von Leu 15—Gastrin I."
Albericio et al. J. Org. Chem. 1990, vol. 55, p. 3730-3743, "Preparation and Application of the 5-(4-(9-Fluorenylmethyloxycarbonyl)aminomethyl-3,5-dimethoxyphenoxy)-valeric Acid (PAL) Handle for the Solid-Phase Synthesis of C-Terminal Peptide Amides under Mild Conditions 1-3."

(Continued)

*Primary Examiner* — Karlheinz R Skowronek
*Assistant Examiner* — Catherine Mader
(74) *Attorney, Agent, or Firm* — Brooks Kushman P.C.

(57) ABSTRACT

Peptide derivatives, their stereoisomers, mixtures thereof and/or their pharmaceutically acceptable salts, a method of obtaining them, pharmaceutical compositions containing them and the use thereof for the treatment, prevention and/or diagnosis of those conditions, disorders and/or pathologies in which the sstr1, sstr2, sstr3, sstr4 and/or sstr5 somatostatin receptors are expressed.

22 Claims, No Drawings

(56) References Cited

OTHER PUBLICATIONS

Wang. Journal of the American Chemical Society Feb. 21, 1973, vol. 95, No. 4, p. 1328-1333 "p-Alkoxybenzyl Alcohol Resin and P-Alkoxybenzyloxycarbonylhydrazide Resin for Solid Phase Synthesis of Protected Peptide Fragments."

15 Burgus et al. PNAS USA Mar. 1973, vol. 70, No. 3, p. 684-688, "Primary Structure of Somatostatin, A Hypothalamic Peptide That Inhibits the Secretion of Pituitary Growth Hormone."

Strowski et al. Endocrinology 2000, vol. 141. No. 1, p. 111-117, "Somatostatin Inhibits Insulin and Glucagon Secretion via Two Receptor Subtypes: An in Vitro Study of Pancreatic Islets from Somatorstatin Receptor 2 Knockout Mice."

Jung et al. Laboratory Investigation 2006, vol. 86, p. 477-489, "A potential role of somatostatin and its receptor SSTR4 in the migration of hepatic oval cells."

Brown et al. J. Pysiol. 1978, vol. 277, p. 1-14, "Structure-Activity Relationships of Eighteen Somatostatin Analogues on Gastric Secretion."

Khare et al. The FASEB Journal Feb. 1999, vol. 13, p. 387-394, "Differential regulation of somatostatin receptor types 1-5 in rat aorta after angioplasty."

Reubi. Endocrine Reviews 2003, vol. 24, No. 4, p. 389-427, "Peptide Receptors as Molecular Targets for Cancer Diagnosis and Therapy."

Tulipano et al. European Journal of Endocrinology 2007, vol. 156, p. S3-S11, "Novel insights in somatostatin receptor physiology."

Lamberts et al. European Journal of Endocrinology 2002, vol. 146, p. 701-705, "New somatostatin analogs: will they fufil old promises?"

Saveanu et al. The Journal of Clinical Endocrinology and Metabolism 2001, vol. 86, No. 1, p. 140-145, "BIM-23244, a Somatostatin Receptor Subtype 2- and 5-Selective Analog with Enganced Efficacy in Suppressing Growth Hormone (GH) from Octreotide-Resistant Human GH-Secreting Adenomas."

Pawlikowski et al. Neuroendocrinology Letters Feb.-Apr. 2003, vol. 24, No. 1/2, p. 21-27, "Perspectives of new potential therapeutic applications of somatostatin analogs."

Bocci et al. European Journal of Clinical Investigation 2007, vol. 37, p. 700-708, "In vitro antiangiogenic activity of selective somatostatin subtype-I receptor agonists."

D'Addona et al. J. Med. Chem. 2008, vol. 51, No. 3, p. 512-520, "Novel sst-Selective Somatostatin Dicarba-Analogues: Analogues: Synthesis and Conformation # Affinity Relationships."

Dirkx et al. Reunion D'Anvers Jun. 1979, p. 1043-1044, "Conformational Studies on somatostatin : a synthesis."

Gilon et al. Biopolymers 1980, vol. 19, p. 341-352, "Conformational Analysis of Somatostatin and Selected Analogs in Oriented Polyoxythylene by Infrared Dichroism."

Hansson et al. The Prostate 2002, vol. 53, p. 50-59, "Expression of Somatostatin Receptor Subtypes 2 and 4 in Human Benign Prostatic Hyperplasia and Prostatic Cancer."

Hirst et al. Regulatory Peptides 1980, vol. 1, p. 97-113, "Structure-Activity Studies with Somatostatin: The Role of Tryptophan in Position 8."

Hirst et al. Regulatory Peptides 1984, vol. 8, p. 267-271, "Structure-Activity studies with somatostatin: role of lysine in positions 4 and 9 for gastric activity."

Joint Commussion on Biochemical Nomenclature Eur. J. Biochem. 1984, vol. 138, p. 9-37, "Nomenclature and Symbolism for Amino Acids and Peptides."

Janecka et al. J. Peptide Res. 2001, vol. 58, p. 91-107, "Review Somatostatin analogs."

Knappenberg et al. Biochimica et Biophysica Acta. 1982, vol. 700, p. 229-246, "The Conformational Properties of Somatostatin."

Kumar., Neuroscience 2005, vol. 134, p. 525-538, "Expression of somatostatin receptor subtypes (SSTR1-5) in Alzheimer's Disease Brain: An Immunohistochemical Analysis."

Patel et al. Endocrinology 1994, vol. 135, No. 6, p. 2814-2817, "Subtype Selectivity of Peptide Analogs for All Five Human Somatostatin Receptors (hsstr 1-5)."

Patel., Frontiers in Neuroendocrinology 1999, vol. 20, p. 157-198, "Somatostatin and Its Receptor Family."

Qiu et al. World J. Gastroenterol Apr. 7, 2006, vol. 12, No. 13, p. 2011-2015, "Relationship between somatostatin receptor subtype expression and clinicopathology, Ki-67, Bcl-2 and p53 in colorectal cancer."

Rink., Tetrahedron Letter 1987, vol. 28, No. 33, p. 3787-3790, "Solid-Phase Synthesis of Protected Peptide Fragments Using a Trialkoxy-Diphenyl-Methylester Resin."

Tamarlt-Rodriguez et al. 1985, vol. 17, p. 623-625, "Antigenic Specificity of a New Potent Somatostatin Antiserum."

Vaysse et al. Curr. Med. Chem.—Anti-Inflammatory and Anti-Allergy Agents 2005, vol. 4, p. 91-104, "Novel Therpeutic Targets for Somatostatin in Inflammatory Chronic Diseases."

Weckbecker et al. Endocrinology 2002, vol. 143, No. 10, p. 4123-4130, "SOM230: A New Somatostatin Peptidomimetic with Potent Inhibitory Effects on the Growth Hormone/ Insulin-like Growth Factor-I Axis in Rats, Primates, and Dogs."

Weckbecker et al. Nature Reviews Drug Discovery Dec. 2003, vol. 2, p. 999-1017, "Opportunities in Somatostatin Research: Biological, Chemical and Therapeutic Aspects."

Remington, 21st edition, 2005, "The Science and Practice of Pharmacy." 60 Pages.

Smith et al. 1999, 5th edition, 111 Pages, "March's Advanced Organic Chemistry Reactions, Mechanisms, and Structure."

Pawlikowski et al. Neuoendocrinology Letters 2003, Nos. 1/2, vol. 24, p. 21-27, "Perspectives of new potential therapeutic applications of somatostatin analogs."

* cited by examiner

PEPTIDE LIGANDS OF SOMATOSTATIN RECEPTORS

CROSS-REFERENCE TO RELATED APPLICATION

This application is the U.S. national phase of PCT Appln. No. PCT/EP2010/056152 filed May 6, 2010 which claims priority to Spanish application P200901168 filed May 7, 2009, the disclosures of which are incorporated in their entirety by reference herein.

SEQUENCE LISTING

The text file is Sequence_Listing.txt, created Nov. 7, 2011, and of size 13 KB, filed therewith, is hereby incorporated by reference.

FIELD OF THE INVENTION

This invention is within the field of biomedical chemistry. The invention particularly encompasses new peptide ligands of somatostatin receptors. These peptide ligands have a potential application in preventive and/or curative therapies, applied to pathologies in which the somatostatin receptors are expressed, as well as in the diagnosis of diseases in which said receptors are expressed.

BACKGROUND OF THE INVENTION

Somatostatin is a cyclic tetradecapeptide originally isolated in the hypothalamus [Burgus et al., Proc. Natl. Acad. Sci. USA, 1973, 70, 684-688]. The somatostatin regulating mechanism commences by means of binding to the G protein-coupled sstr1, sstr2, sstr3, sstr4 and sstr5 somatostatin receptors [Patel et al., Front. Neuroendocrinol., 1999, 20, 157-198]. They all bind to somatostatin with nanomolar affinity [Patel et al., Endocrinology, 1994, 135, 2814-2817]. The five somatostatin receptors differ in their distribution in tissue and pharmacological properties. The first known action of somatostatin is the inhibition of secretion of the growth hormone via the sstr2 and sstr5 receptors. Furthermore, somatostatin inhibits glucagon secretion through sstr2 and insulin secretion via sstr5 [Strowski et al., 2000, Endocrinology, 141(1), 111-117]. The sstr3, and to a lesser extent, sstr2 receptors seem to be involved in induction of cell apoptosis [Qiu et al., 2006, World Gastroenterol., 12(13), 2011-2015]. In addition, sstr1 and sstr5 have an inhibitory effect on the cell cycle and sstr1 could modulate angiogenesis [Bocci et al., Eur. J. Clin. Invest., 2007, 37(9), 700-708]. The function of sstr4 has been studied less, although recent studies have shown its potential as a therapeutic target in hepatic diseases and prostate cancer [Jung et al., Laboratory Investigation, 2006, 86, 477-489; Hansson et al., Prostate, 2002, 53(1), 50-59].

In clinical practice, somatostatin is used as therapy for the treatment of gastrointestinal bleeding due to esophagogastric varices and as an adjuvant in the treatment of secreting pancreatic fistulae. The lack of side effects is its greatest advantage. Despite its biological profile, one of the drawbacks of somatostatin is its short blood half-life (less than 3 min), which makes continuous endovenous infusion necessary and restricts its use to a hospital level.

The short half-life of somatostatin brought about the development of analogs that present greater stability against enzymatic degradation. Somatostatin analogs which maintain the structure of the original molecule can be found in the state of the art. For example, U.S. Pat. No. 4,211,693 A describes somatostatin analogs in which any of the phenylalanine amino acids has been substituted with para-halogenated or para-methoxylated phenylalanine, and U.S. Pat. No. 4,133,782 A describes somatostatin analogs in which the tryptophan amino acid in position 8 is the D-stereoisomer. Brown et al. also describe primarily analogs with D-amino acids [Brown et al. J Physiol. 1978, 277, 1-14]. Besides these initial proposals for somatostatin analogs from the original molecule, most of the works known in the state of the art relate to analogs of 8 or fewer amino acids [Janecka et al. 2001, J. Pept. Res., 58(2), 91-107; Pawlikowski et al., 2004, Curr. Opin. Pharmacol., 4(6), 608-613].

Octreotide was the first analog developed in clinical practice. It has a structure with a 6-amino acid cycle. Other octreotide analogs which maintain a common structure with a 6-amino acid cycle (lanreotide, vapreotide, pasireotide) can be found in the state of the art. The reduction of the original 12-amino acid cycle of somatostatin to a 6-amino acid cycle restricts the flexibility of the original molecule by limiting interaction with some receptors of the family of sstr1-sstr5 receptors. While somatostatin binds with nanomolar affinity to each of its sstr1, sstr2, sstr3, sstr4 and sstr5 receptors, octreotide, lanreotide and vapreotide only bind with high affinity to the sstr2 receptor, with moderate affinity to the sstr5 receptor, and with moderate-low affinity to sstr3 and they do not bind to the sstr1 and sstr4 receptors [Patel et al., Endocrinology, 1994, 135(6), 2814-2817]. In the example of pasireotide, the interaction with the sstr4 receptor is lost and the affinity for the sstr2 receptor is an order of magnitude lower [Weckbecker et al., Endocrinology, 2002, 143, 4123-4130].

The identification of different expression profiles of the five somatostatin receptors in target organs of somatostatin explains the limited efficacy of treatments with octreotide, lanreotide and vapreotide in pathologies in which the sstr2 receptor is under-expressed [Khare et al., Faseb J., 1999, 13(2), 387-394].

The use of these 3 analogs has been approved only for a limited number of clinical applications, such as acromegaly, metastatic carcinoid tumor, VIPomas, diarrhea, bleeding of esophageal varices and perioperative protection in pancreatic surgery. Taking into account the wide range of pathologies in which the expression of somatostatin receptors has been identified [Pawlikowski et al., Neuro Endocrinol Lett, 2003, 24 (1-2), 21-27; Vaysse et al., Curr. Med. Chem., 2005, 4, 91-104; Reubi et al., Endocr. Rev., 2003, 24(4), 389-427; Kumar et al., Neuroscience, 2005, 134(2), 525-538] these known analogs solve a small area of possible applications.

In this context of clinical interest for new somatostatin analogs with a high affinity for several or all the receptors thereof and of new applications of somatostatin and its analogs [Tulipano et al., Eur. J. Endocrinol., 2007, 156 Suppl 1, S3-S11; Lamberts et al., Eur. J. Endocrinol., 2002, 146(5), 701-705], the heterogeneous expression of the sstr2 and sstr5 receptors in secreting adenomas of the growth hormone and their treatment with bispecific analogs has demonstrated better control of growth hormone hypersecretion with respect to treatment with octreotide and lanreotide, with preferential affinity for the sstr2 receptor, with an inhibitory concentration $IC_{50}$ of 12 to 18 times greater than sstr5 [Savenau et al., J. Clin. Endocrinol. Metab., 2001, 86, 140-145].

Therefore, there is still a need to find new synthetic somatostatin analogs for the treatment of those pathologies which present expressed somatostatin receptors sstr1, sstr2, sstr3, sstr4 or sstr5 and which present greater stability in blood than somatostatin.

The new somatostatin analogs must present a broader profile of interaction with the somatostatin receptors, if possible a universal profile of interaction with the 5 sstr1 to sstr5 receptors, or which is at least specific for those receptors with which the analogs already known in the state of the art do not interact, such as the sstr1, sstr4, and sstr3 receptors.

DESCRIPTION OF THE INVENTION

The present invention provides a solution to the aforementioned problems. It has surprisingly been found that certain modifications with non-natural or derivatized amino acids improve the selectivity or maintain a profile of universal interaction with the sstr1, sstr2, sstr3, sstr4 and sstr5 receptors. It has particularly been found that the substitution of phenylalanine of the original sequence with aromatic synthetic amino acids with alkyl substituents, the derivatization of the amino group of the lysine side chain, the substitution of cysteines with allylglycines or the substitution of tryptophan with quinolylalanine cause the resulting peptides with one or several of these modifications to present stabilities in serum, gastric fluid and intestinal fluid that are greater than the stabilities of somatostatin and to interact with the 5 sstr1 to sstr5 receptors or combinations of several of these receptors. The peptides of the present invention are also useful for the treatment, prevention and/or diagnosis of those conditions, disorders and/or pathologies in which the sstr1 to sstr5 somatostatin receptors are expressed.

DEFINITIONS

The meanings of some terms and expressions as they are used in the context of the invention are included for the purpose of aiding understanding of the present invention.

In the present description, the abbreviations used for amino acids follow the rules of the IUPAC-IUB Joint Commission on Biochemical Nomenclature specified in Eur. J. Biochem., 1984, 138:9-37 and in J. Biol. Chem., 1989, 264:633-673.

Thus, for example, Gly represents $NH_2$—$CH_2$—COOH, Gly- represents $NH_2$—$CH_2$—CO—, -Gly represents —NH—$CH_2$—COOH and -Gly- represents —NH—$CH_2$—CO—. Therefore, the dash, which represents the peptide bond, eliminates the OH from the 1-carboxyl group of the amino acid (represented herein in the conventional non-ionized form) when it is located to the right of the symbol, and it eliminates the H from the 2-amino group of the amino acid when it is located to the left of the symbol; both modifications can be applied to one and the same symbol.

The term "non-cyclic aliphatic group" is used in the present invention to include linear or branched alkyl, alkenyl and alkynyl groups.

The term "alkyl group" relates to a linear or branched saturated group having between 1 and 24, preferably between 1 and 16, more preferably between 1 and 14, even more preferably between 1 and 12, still more preferably 1, 2, 3, 4, 5 or 6 carbon atoms and which is bound to the rest of the molecule by means of a single bond, including, by way of non-limiting example, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and the like.

The term "alkenyl group" relates to a linear or branched group having between 2 and 24, preferably between 2 and 16, more preferably between 2 and 14, even more preferably between 2 and 12, still more preferably 2, 3, 4, 5 or 6 carbon atoms, with one or more carbon-carbon double bonds, preferably with 1, 2 or 3 conjugated or unconjugated carbon-carbon double bonds, which is bound to the rest of the molecule by means of a single bond, including, by way of non-limiting example, vinyl (—$CH_2$=$CH_2$), allyl (—$CH_2$–CH=$CH_2$), oleyl, linoleyl group and the like.

The term "alkynyl group" relates to a linear or branched group having between 2 and 24, preferably between 2 and 16, more preferably between 2 and 14, even more preferably between 2 and 12, still more preferably 2, 3, 4, 5 or 6 carbon atoms with one Or more carbon-carbon triple bonds, preferably 1, 2 or 3 conjugated or unconjugated carbon-carbon triple bonds, which is bound to the rest of the molecule by means of a single bond, including, by way of non-limiting example, the ethinyl group, 1-propinyl group, 2-propinyl group, 1-butinyl group, 2-butinyl group, 3-butinyl group, pentinyl group, for example 1-pentinyl group, and the like. The alkynyl groups can also contain one or more carbon-carbon double bonds, including by way of non-limiting example, the but-1-en-3-inyl, pent-4-en-1-inyl group and the like.

The term "alicyclic group" is used in the present invention to include, by way of non-limiting example, cycloalkyl or cycloalkenyl or cycloalkynyl groups.

The term "cycloalkyl" relates to a saturated mono- or polycyclic aliphatic group having between 3 and 24, preferably between 3 and 16, more preferably between 3 and 14, even more preferably between 3 and 12, still more preferably 3, 4, 5 or 6 carbon atoms and which is bound to the rest of the molecule by means of a single bond, including, by way of non-limiting example, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and the like.

The term "cycloalkenyl" relates to a non-aromatic mono- or polycyclic aliphatic group having between 5 and 24, preferably between 5 and 16, more preferably between 5 and 14, even more preferably between 5 and 12, still more preferably 5 or 6 carbon atoms, with one or more carbon-carbon double bonds, preferably 1, 2 or 3 conjugated or unconjugated carbon-carbon double bonds, and which is bound to the rest of the molecule by means of a single bond, including, by way of non-limiting example, the cyclopent-1-en-1-yl group and the like.

The term "cycloalkynyl" relates to a non-aromatic mono- or polycyclic aliphatic group having between 8 and 24, preferably between 8 and 16, more preferably between 8 and 14, even more preferably between 8 and 12, still more preferably 8 or 9 carbon atoms, with one or more carbon-carbon triple bonds, preferably 1, 2 or 3 conjugated or unconjugated carbon-carbon triple bonds, and which is bound to the rest of the molecule by means of a single bond, including, by way of non-limiting example, the cyclooct-2-en-1-yl group and the like. The cycloalkynyl groups can also contain one or more carbon-carbon double bonds, including by way of non-limiting example, the cyclooct-4-in-2-inyl group and the like The term "aryl group" relates to an aromatic group having between 6 and 30, preferably between 6 and 18, more preferably between 6 and 10, even more preferably 6 or 10 carbon atoms, comprising 1, 2, 3 or 4 aromatic rings, linked by means of a carbon-carbon bond or fused, including, by way of non-limiting example, phenyl, naphthyl, diphenyl, indenyl, phenanthryl or anthranyl among others; or to an aralkyl group.

The term "aralkyl group" relates to an alkyl group substituted with an aromatic group, having between 7 and 24 carbon atoms and including, by way of non-limiting example, —$(CH_2)_{1-6}$-phenyl, —$(CH_2)_{1-6}$-(1-naphthyl), —$(CH_2)_{1-6}$-(2-naphthyl), —$(CH_2)_{1-6}$—CH(phenyl)$_2$ and the like.

The term "heterocyclyl group" relates to a hydrocarbon ring having 3-10 members, in which one or more of the atoms of the ring, preferably 1, 2 or 3 of the atoms of the ring, is an element other than carbon, such as for example nitrogen, oxygen or sulfur and which can be saturated or unsaturated. For the purposes of this invention, the heterocycle can be a cyclic, monocyclic, bicyclic or tricyclic system, which can include fused ring systems; and the nitrogen, carbon or sulfur atoms can optionally be oxidized in the heterocyclyl radical; the nitrogen atom can optionally be quaternized; and the heterocyclyl radical can be partially or completely saturated or can be aromatic. More preferably, the term heterocyclic relates to a ring having 5 or 6 members. Examples of saturated heterocyclyl groups are dioxane, piperidine, piperazine, pyrrolidine, morpholine and thiomorpholine. Examples of aromatic heterocyclyl groups, also known as heteroaromatic groups, are pyridine, pyrrole, furan, thiophene, benzofuran, imidazoline, quinoleine, quinoline, pyridazine and naphthyridine.

The term "heteroarylalkyl group" relates to an alkyl group substituted with a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, by way of non-limiting example, $-(CH_2)_{1-6}$-imidazolyl, $-(CH_2)_{1-6}$-triazolyl, $-(CH_2)_{1-6}$-thienyl, $-(CH_2)_{1-6}$-furyl, $-(CH_2)_{1-6}$-pyrrolidinyl and the like.

As is understood in this technical field, there can be a certain degree of substitution in the previously defined groups. Therefore, there can be substitution in the groups of the present invention where this is explicitly indicated. The references herein to substituted groups in the groups of the present invention indicate that the specified radical can be substituted in one or more available positions with one or more substituents, preferably in 1, 2 or 3 positions, more preferably in 1 or 2 positions, still more preferably in 1 position. Said substituents include, by way of non-limiting example, $C_1$-$C_4$ alkyl; hydroxyl; $C_1$-$C_4$ alcoxyl; amino; $C_1$-$C_4$ aminoalkyl; $C_1$-$C_4$ carbonyloxyl; $C_1$-$C_4$ oxycarbonyl; halogen such as fluorine, chlorine, bromine and iodine; cyano; nitro; azido; $C_1$-$C_4$ alkylsulfonyl; thiol; $C_1$-$C_4$ alkylthio; aryloxyl such as phenoxyl; $-NR_b(C=NR_b)NR_bR_c$; where $R_b$ and $R_c$ are independently selected from the group consisting of H, $C_1$-$C_4$ alkyl, $C_2$-$C_4$ alkenyl, $C_2$-$C_4$ alkynyl, $C_3$-$C_{10}$ cycloalkyl, $C_6$-$C_{18}$ aryl, $C_7$-$C_{17}$ aralkyl, heterocyclyl having 3-10 members or a protecting group of the amino group.

COMPOUNDS OF THE INVENTION

The compounds of the invention are defined by general formula (I)

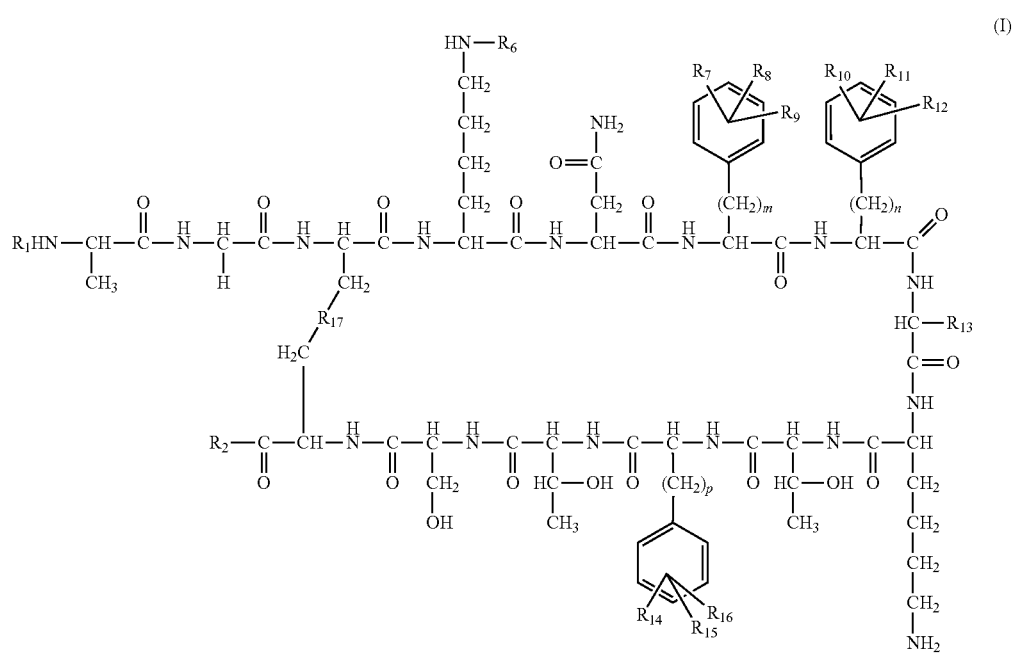

their stereoisomers, mixtures thereof and/or their pharmaceutically acceptable salts, wherein:

$R_1$ is selected from the group consisting of H, a substituted or unsubstituted non-cyclic aliphatic group, a substituted or unsubstituted alicyclyl group, a substituted or unsubstituted heterocyclyl group, a substituted or unsubstituted heteroarylalkyl group, a substituted or unsubstituted aryl group, a substituted or unsubstituted aralkyl group, a polyethylene glycol polymer, a chelating agent and $R_5$—CO—;

$R_2$ is selected from the group consisting of —$NR_3R_4$, —$OR_3$ and —$SR_3$;

$R_6$ is selected from the group consisting of H, acetyl, trifluoroacetyl, isopropyl, palmitoyl, allyloxycarbonyl, 2-chlorobenzyl, formyl, N-[1-(4,4-dimethyl-2,6-dioxocyclohex-1-ylidene)ethyl] and benzyloxycarbonyl;

$R_7$, $R_8$, $R_9$, $R_{10}$, $R_{11}$, $R_{12}$, $R_{14}$, $R_{15}$ and $R_{16}$ are selected independently from one another from the group consisting of H and a non-cyclic aliphatic group;

m is an integer selected from between 0 and 6 with the condition that when $R_7$, $R_8$ and $R_9$ are H, then m is different from 0;

n is an integer selected from between 0 and 6 with the condition that when $R_{10}$, $R_{11}$ and $R_{12}$ are H, then n is different from 0;

p is an integer selected from between 0 and 6 with the condition that when $R_{14}$, $R_{15}$ and $R_{16}$ are H, then p is different from 0;

$R_{13}$ is selected from the group consisting of L-(3-quinolyl)methyl, D-(3-quinolyl)methyl, L-(3-indolyl)methyl and D-(3-indolyl)methyl;

$R_{17}$ is selected from the group consisting of —S—S—, —CH$_2$—CH$_2$— and —CH=CH—;

$R_3$ and $R_4$ are independently selected from the group consisting of H, a substituted or unsubstituted non-cyclic aliphatic group, a substituted or unsubstituted alicyclyl group, a substituted or unsubstituted heterocyclyl group, a substituted or unsubstituted heteroarylalkyl group, a substituted or unsubstituted aryl group, a substituted or unsubstituted aralkyl group and a polymer;

$R_5$ is selected from the group consisting of H, a substituted or unsubstituted non-cyclic aliphatic group, a substituted or unsubstituted alicyclyl group, a substituted or unsubstituted aryl group, a substituted or unsubstituted aralkyl group, a substituted or unsubstituted heterocyclyl group and a substituted or unsubstituted heteroarylalkyl group;

with the condition that when $R_6$, $R_7$, $R_8$, $R_9$, $R_{10}$, $R_{11}$, $R_{12}$, $R_{14}$, $R_{15}$ and $R_{16}$ are all equal to H, n, m and p are equal to 1 and $R_{13}$ is equal to L-(3-indolyl)methyl or to D-(3-indolyl)methyl, $R_{17}$ is not equal to —S—S—.

The $R_1$ and $R_2$ groups are bound at the amino-terminal (N-terminal) and carboxy-terminal (C-terminal) ends of the peptide sequences, respectively.

According to a preferred embodiment of the present invention $R_1$ is selected from the group consisting of H, a polymer of general formula (II)

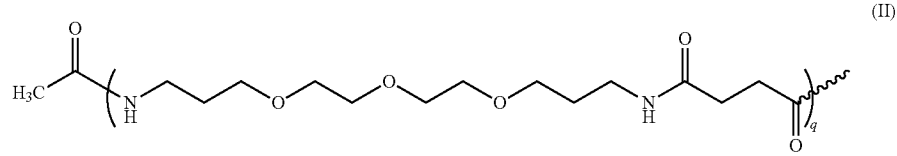

(II)

where q ranges between 1 and 5, and $R_5$—CO—, where $R_5$ is selected from the group consisting of substituted or unsubstituted $C_1$-$C_{24}$ alkyl radical, substituted or unsubstituted $C_2$-$C_{24}$ alkenyl radical, substituted or unsubstituted $C_2$-$C_{24}$ alkynyl radical, substituted or unsubstituted $C_3$-$C_{24}$ cycloalkyl radical, substituted or unsubstituted $C_5$-$C_{24}$ cycloalkenyl radical, substituted or unsubstituted $C_8$-$C_{24}$ cycloalkynyl radical, substituted or unsubstituted $C_6$-$C_{30}$ aryl radical, substituted or unsubstituted $C_7$-$C_{24}$ aralkyl radical, a substituted or unsubstituted heterocyclyl radical having 3-10 ring members, a substituted or unsubstituted heteroarylalkyl radical having 2 to 24 carbon atoms and having 1 to 3 atoms other than carbon where the alkyl chain is of 1 to 6 carbon atoms. More preferably, $R_1$ is selected from H, acetyl, tert-butanoyl, hexanoyl, 2-methylhexanoyl, cyclohexanecarboxyl, octanoyl, decanoyl, lauroyl, myristoyl, palmitoyl, stearoyl, behenyl, oleoyl and linoleoyl. Even more preferably, $R_1$ is H, acetyl, hexanoyl, octanoyl, lauroyl, myristoyl or palmitoyl.

According to another preferred embodiment, $R_1$ is a chelating agent optionally complexed with a detectable element or a radiotherapeutic element. Chelating agent is understood as a group that is capable of forming coordination complexes with the detectable element or the radiotherapeutic element. Preferably, the chelating agent is a group capable of forming complexes with metal ions, more preferably selected from the group consisting of DOTA, DTPA, TETA or derivatives thereof. The chelating agent can be bound directly or through a linker.

Detectable element is understood as any element, preferably a metal ion, displaying a detectable property in an in vivo diagnostic technique. Radiotherapeutic element is understood as any element emitting α radiation, β radiation, or γ radiation.

According to another preferred embodiment, $R_2$ is —NR$_3$R$_4$, —OR$_3$ or —SR$_3$ where $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, a substituted or unsubstituted heterocyclyl having 3-10 ring members, and a substituted or unsubstituted heteroarylalkyl group having 2 to 24 carbon atoms and having 1 to 3 atoms other than carbon where the alkyl chain is of 1 to 6 carbon atoms and a polymer of general formula (II) where q ranges between 1 and 5. Optionally, $R_3$ and $R_4$ can be bound by means of a saturated or unsaturated carbon-carbon bond, forming a cycle with the nitrogen atom. More preferably, $R_2$ is —NR$_3$R$_4$ or —OR$_3$, where $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{10}$ cycloalkyl, substituted or unsubstituted $C_6$-$C_{15}$ aryl and a substituted or unsubstituted heterocyclyl of 3-10 members, a substituted or unsubstituted heteroarylalkyl group with a ring having 3 to 10 members and an alkyl chain of 1 to 6 carbon atoms and a polymer of general formula (II) where q ranges between 1 and 5. More preferably, $R_3$ and $R_4$ are selected from the group consisting of H, methyl, ethyl, hexyl, dodecyl or hexadecyl. Even more preferably, $R_3$ is H and $R_4$ is selected from the group consisting of H, methyl, ethyl, hexyl, dodecyl or hexadecyl. According to an even more preferred embodiment, $R_2$ is selected from —OH and —NH$_2$.

According to another preferred embodiment, $R_7$, $R_8$ and $R_9$ are equal to one another and are in an ortho-, para-, ortho- configuration or a meta-, para-, meta-configuration, $R_{10}$, $R_{11}$ and $R_{12}$ are equal to one another and are in an ortho-, para-, ortho-configuration or a meta-, para-, meta-configuration, and $R_{14}$, $R_{15}$ and $R_{16}$ are equal to one another and are in an ortho-, para-, ortho-configuration or a meta-, para-, meta-configuration, more preferably, $R_7$, $R_8$, $R_9$, $R_{10}$, $R_{11}$, $R_{12}$, $R_{14}$, $R_{15}$ and $R_{16}$ are selected from the group consisting of H and $C_1$-$C_{24}$ alkyl, even more preferably they are selected from the group consisting of H and $C_1$-$C_6$ alkyl, and still more preferably they are selected from the group consisting of H, methyl and ethyl.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is H, $R_7$, $R_8$ and $R_9$ are methyl and are in an ortho-, para-, ortho-configuration or a meta-, para-, meta-configuration, m is 0 or 1, $R_{10}$, $R_{11}$, $R_{12}$, $R_{14}$, $R_{15}$ and $R_{16}$ are H, n and p are equal to 1, $R_{13}$ is selected from the group consisting of L-(3-indolyl)methyl and D-(3-indolyl)methyl and $R_{17}$ is —S—S—.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is H, $R_{10}$, $R_{11}$ and $R_{12}$ are methyl and are in an ortho-, para-, ortho-configuration or a meta-, para-, meta-configuration, n is 0 or 1, $R_7$, $R_8$, $R_9$, $R_{14}$, $R_{15}$ and $R_{16}$ are H, m and p are equal to 1, $R_{13}$ is selected from the group consisting of L-(3-indolyl)methyl and D-(3-indolyl)methyl and $R_{17}$ is —S—S—.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is H, $R_{14}$, $R_{15}$ and $R_{16}$ are methyl and are in an ortho-, para-, ortho-configuration or a meta-, para-, meta-configuration, p is 0 or 1, $R_7$, $R_8$, $R_9$, $R_{10}$, $R_{11}$ and $R_{12}$ are H, m and n are equal to 1, $R_{13}$ is selected from the group consisting of L-(3-indolyl)methyl and D-(3-indolyl)methyl and $R_{17}$ is —S—S—.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is H, $R_7$, $R_8$, $R_9$, $R_{10}$, $R_{11}$ and $R_{12}$ are methyl and are in an ortho-, para-, ortho-configuration or a meta-, para-, meta-configuration, m and n are 0 or 1, $R_{14}$, $R_{15}$ and $R_{16}$ are H, p is equal to 1, $R_{13}$ is selected from the group consisting of L-(3-indolyl)methyl and D-(3-indolyl)methyl and $R_{17}$ is —S—S—.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is H, $R_7$, $R_8$, $R_9$, $R_{14}$, $R_{15}$ and $R_{16}$ are methyl and are in an ortho-, para-, ortho-configuration or a meta-, para-, meta-configuration, m and p are 0 or 1, $R_{10}$, $R_{11}$ and $R_{12}$ are H, n is equal to 1, $R_{13}$ is selected from the group consisting of L-(3-indolyl)methyl and D-(3-indolyl)methyl and $R_{17}$ is —S—S—.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is H, $R_{10}$, $R_{11}$, $R_{12}$, $R_{14}$, $R_{15}$ and $R_{16}$ are methyl and are in an ortho-, para-, ortho-configuration or a meta-, para-, meta-configuration, n and p are 0 or 1, $R_7$, $R_8$ and $R_9$ are H, m is equal to 1, $R_{13}$ is selected from the group consisting of L-(3-indolyl)methyl and D-(3-indolyl)methyl and $R_{17}$ is —S—S—.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is selected from the group consisting of acetyl, palmitoyl, trifluoroacetyl, isopropyl, allyloxycarbonyl, 2-chlorobenzyl, N-[1-(4,4-dimethyl-2,6-dioxocyclohex-1-ylidene)ethyl], $R_7$, $R_8$, $R_9$, $R_{10}$, $R_{11}$, $R_{12}$, $R_{14}$, $R_{15}$ and $R_{16}$ are H, m, n and p are equal to 1, $R_{13}$ is selected from the group consisting of L-(3-indolyl)methyl and D-(3-indolyl)methyl and $R_{17}$ is —S—S—.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is H, $R_7$, $R_8$, $R_9$, $R_{10}$, $R_{11}$, $R_{12}$, $R_{14}$, $R_{15}$ and $R_{16}$ are H, m, n and p are equal to 1, $R_{13}$ is selected from the group consisting of L-(3-quinolyl)methyl and D-(3-quinolyl)methyl and $R_{17}$ is —S—S—.

According to another embodiment of the present invention, $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from H, methyl, ethyl, hexyl, dodecyl and hexadecyl, $R_6$ is H, $R_7$, $R_8$, $R_9$, $R_{10}$, $R_{11}$, $R_{12}$, $R_{14}$, $R_{15}$ and $R_{16}$ are H, m, n and p are equal to 1, $R_{13}$ is selected from the group consisting of L-(3-indolyl)methyl and D-(3-indolyl)methyl and $R_{17}$ is —CH═CH—.

The compounds of the present invention can exist as stereoisomers or mixtures of stereoisomers; for example, the amino acids forming them can have an L-, D-configuration, or can be racemic independently of one another. Therefore, it is possible to obtain isomeric mixtures, as well as racemic mixtures or diastereomeric mixtures, or pure diastereomers or enantiomers, depending on the number of asymmetric carbons and on which isomers or isomeric mixtures are present. The preferred structures of the compounds of the invention are pure isomers, i.e., a single enantiomer or diastereomer.

For example, unless otherwise indicated, it is understood that the amino acid is L or D, or racemic or non-racemic mixtures of both. The preparation processes described in the present document allow the person skilled in the art to obtain each of the stereoisomers of the compound of the invention by means of choosing the amino acid with the suitable configuration.

The pharmaceutically acceptable salts of the compounds provided in the present invention are also within the scope thereof. The term "pharmaceutically acceptable salts" means a salt that is recognized for use in animals and more particularly in humans, and it includes the salts used to form addition salts of bases, inorganic bases, such as, by way of non-limiting example, lithium, sodium, potassium, calcium, magnesium, manganese, copper, zinc or aluminum, among others, or organic bases, such as, by way of non-limiting example, ethylamine, diethylamine, ethylenediamine, ethanolamine, diethanolamine, arginine, lysine, histidine or piperazine among others, or addition salts of acids, organic acids, such as by way of non-limiting example, acetate, citrate, lactate, malonate, maleate, tartrate, fumarate, benzoate, aspartate, glutamate, succinate, oleate, trifluoroacetate, oxalate, pamoate or gluconate among others, or inorganic acids, such as by way of non-limiting example, chloride, sulfate, borate or carbonate, among others. The nature of the salt is not critical provided that it is pharmaceutically acceptable. The pharmaceutically acceptable salts of the peptides of the invention can be obtained by conventional methods well-known in the state of the art [Berge S. M. et al., J. Pharm. Sci. 1977, 66, 1-19].

Another aspect of the present invention relates to a compound of general formula (I), their stereoisomers, mixtures thereof and/or their pharmaceutically acceptable salts, as described in the present invention, for the treatment, prevention and/or diagnosis of those conditions, disorders and/or pathologies in which the sstr1, sstr2, sstr3, sstr4 and/or sstr5 somatostatin receptors are expressed.

In a more particular aspect, the present invention relates to a compound of general formula (I), their stereoisomers, mixtures thereof and/or their pharmaceutically acceptable salts, as described in the present invention, for the treatment, prevention and/or diagnosis of those conditions, disorders and/or pathologies selected from the group consisting of acromegaly, symptomatic treatment of gastroenteropancreatic neuroendocrine tumors, diarrhea, cancer, tumors, neurodegenerative diseases, ocular diseases, immune system pathologies, inflammation, infections, esophageal varices, pain, wound healing, tissue regeneration, chronic pancreatitis, hypertrophic pulmonary osteoarthropathy and thyrotrophic adenoma.

In a more particular aspect, the present invention relates to a compound of general formula (I), their stereoisomers, mixtures thereof and/or their pharmaceutically acceptable salts, as described in the present invention, for the treatment, prevention and/or diagnosis of those conditions, disorders and/or pathologies selected from the group consisting of acromegaly, inflammation, infections, esophageal varices, neuropathic pain, wound healing, tissue regeneration, chronic pancreatitis, hypertrophic pulmonary osteoarthropathy, thyrotrophic adenoma, grade 3-4 diarrhea, diarrhea associated with radiotherapy and/or chemotherapy treatment, symptomatic treatment of carcinoid syndrome or VIPomas, endocrine cancer, pancreatic cancer, colorectal cancer, breast cancer, ovarian cancer, prostate cancer, thyroid cancer, lung cancer, gastric cancer, hepatocellular carcinoma, Alzheimer's disease, arthritis, allergies, Lupus erythematosus, lymphoproliferative disorder, diabetic retinopathy, macular edema, Graves' ophthalmopathy, Cushing's syndrome, restenosis, angiogenesis, hyperthyroidism, hypothyroidism, hyperinsulinemia, psoriasis, hypercalcemia, Paget's disease, caquexia, and Zollinger-Ellison syndrome.

In a more particular aspect, the treatment, prevention and/or diagnosis with the compounds of the present invention is performed by means of a local or systemic application, such as, by way of non-limiting example by topical, oral or parenteral route. In the context of the present invention, the term "parenteral" includes nasal, auricular, ophthalmic, vaginal, rectal route, subcutaneous, intradermal, intravascular injections, such as, for example, intravenous, intramuscular, intravitreous, intraspinal, intracranial, intraarticular, intrathecal and intraperitoneal injections, as well as any other similar injection or infusion technique.

Preparation Processes

The compounds of the invention, their stereoisomers or their pharmaceutically acceptable salts can be synthesized according to conventional methods known in the state of the art.

In an embodiment of the present invention, the compounds are synthesized by means of solution or solid phase peptide synthesis methods.

The solid phase synthesis methods are described for example in [Stewart J. M. and Young J. D., 1984, "Solid Phase Peptide Synthesis, 2nd edition" Pierce Chemical Company, Rockford, Ill.; Bodanzsky M., and Bodanzsky A., 1984 "The practice of Peptide Synthesis" Springer Verlag, New Cork; Lloyd-Williams P., Albericio F. and Giralt E. (1997) "Chemical Approaches to the Synthesis of Peptides and Proteins" CRC, Boca Raton, Fla., USA]. Solution synthesis methods and combinations of the solution and solid phase synthesis methods or enzymatic synthesis are described in [Kullmann W. et al., J. Biol. Chem., 1980, 255, 8234-8238].

In an embodiment of the present invention, the compounds of formula (I) are prepared by means of a method comprising the steps of:
1. Solid phase synthesis
2. Cleaving the peptide from the polymer support, preferably by means of acid treatment
3. Cycling the peptide in solution
4. If needed, eliminating the protecting groups, preferably with trifluoroacetic acid or alternatively
1. Solid phase synthesis
2. Solid phase cycling
3. Cleaving the peptide from the polymer support and simultaneously eliminating the protecting groups, preferably by means of treatment with trifluoroacetic acid.

Preferably, the C-terminal end is bound to a solid support and the process is developed in solid phase and therefore comprises coupling an amino acid with the N-terminal end protected and the C-terminal end free on an amino acid with the N-terminal end free and the C-terminal end bound to a polymer support; eliminating the protecting group from the N-terminal end; and repeating this sequence as many times as needed to thus obtain a tetradecapeptide, followed finally by cleaving the synthesized peptide from the original polymer support.

The functional groups of the amino acid side chains are maintained suitably protected with temporary or permanent protecting groups throughout synthesis, and they can be deprotected simultaneously or orthogonally to the process of cleaving the peptide from the polymer support.

Alternatively, the solid phase synthesis can be performed by means of a convergent strategy by coupling a peptide fragment on the polymer support or on a peptide fragment previously bound to the polymer support. Convergent synthesis strategies are well known by persons skilled in the art and are described by Lloyd-Williams P. et al. in Tetrahedron 1993, 49, 11065-11133.

The process can comprise the additional steps of deprotecting the N-terminal and C-terminal ends and/or cleaving the peptide from the polymer support in an indistinct order, using standard processes and conditions known in the art, after which the functional groups of said ends can be modified. The optional modification of the N-terminal and C-terminal ends can be performed with the peptide of formula (I) anchored to the polymer support or once the peptide has been cleaved from the polymer support.

Optionally, $R_1$ can be introduced by means of reacting the N-terminal end of the peptide of the invention with an $R_1$—Z compound, where $R_1$ has the meaning described above and Z is a leaving group, such as, by way of non-limiting example, the tosyl group, the mesyl group and halogen groups, among others; by means of a nucleophilic substitution reaction, in the presence of a suitable base and solvent and where said fragments present the functional groups which do not participate in the formation of the N—C bond suitably protected with temporary or permanent protecting groups. $R_1$ can also be introduced by means of reacting the N-terminal end of the compound of the invention with an $R_5COOH$ group or the esters, acid halides or anhydride thereof.

Optionally and/or additionally, the $R_2$ radicals can be introduced by means of reacting an $HR_2$ compound, where $R_2$ is —$OR_3$, —$NR_3R_4$ or —$SR_3$, with a complementary fragment corresponding with the peptide of formula (I) in which $R_2$ is —OH in the presence of a suitable solvent and a base such as, for example, N,N-diisopropylethylamine (DIEA) or triethylamine or an additive such as, for example, 1-hydroxybenzotriazole (HOBt) or 1-hydroxyazabenzotriazole (HOAt) and a dehydrating agent, such as for example a carbodiimide, a uronium salt, a phosphonium salt or an amidinium salt, among others, to thus obtain a peptide according to the invention of general formula (I), where said fragments present the functional groups which do not participate in the formation of the N—C, O—C or S—C bond suitable protected with temporary or permanent protecting groups, or alternatively other $R_2$ radicals can be introduced by means of incorporating simultaneously to the process of cleaving the peptide from the polymer support.

A person skilled in the art will easily understand that the steps of deprotecting/cleaving the C-terminal and N-terminal ends and the subsequent derivatization thereof can be performed in an indistinct order, according to processes known in the art [Smith M. B. and March J., 1999 "March's Advanced Organic Chemistry Reactions, Mechanisms and Structure", 5th Edition, John Wiley & Sons, 2001].

The term "protecting group" relates to a group which blocks an organic functional group and which can be removed under controlled conditions. The protecting groups, their relative reactivities and the conditions in which they remain inert are known by the person skilled in the art.

Examples of representative protecting groups for the amino group are the amides, such as amide acetate, amide benzoate, amide pivalate; carbamates, such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethoxycarbonyl (Troc), 2-(trimethylsilyl)ethoxycarbonyl (Teoc), 9-fluorenylmethoxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl] (Dde), 1-(4,4-dimethyl-2,6-dioxocyclohexylidene)-3-methyl-butyl (ivDde), 1-(1-adamantyl)-1-methylethoxy-carbonyl (Adpoc), among others; preferably, Boc or Fmoc.

Examples of representative protecting groups for the carboxyl group are the esters, such as the tert-butyl (tBu) ester, allyl (All) ester, triphenylmethyl ester (trityl ester, Trt), cyclohexyl (cHx) ester, benzyl (Bzl) ester, ortho-nitrobenzyl ester, para-nitrobenzyl ester, para-methoxybenzyl ester, trimethylsilylethyl ester, 2-phenylisopropyl ester, fluorenylmethyl (Fm) ester, 4-(N-[1-(4,4-dimethyl-2,6-dioxocyclohexylidene)-3-methylbutyl]amino)benzyl (Dmab) ester, among others; preferred protecting groups of the invention are All, tBu, cHex, Bzl and Trt esters.

The trifunctional amino acids can be protected during the synthetic process with temporary or permanent protecting groups orthogonal to the protecting groups of the N-terminal and C-terminal ends. The amino group protecting groups described above are used to protect the amino group of the lysine side chain, the tryptophan side chain can be protected with any of the amino group protecting groups described above, or it may not be protected, the serine and threonine side chain is protected with tert-butyl (tBu) ester, the cysteine side chain is protected with a protecting group selected from the group consisting of trityl and acetamidomethyl and the asparagine side chain can be protected with a protecting group selected from the group consisting of methoxytrityl, trityl and xanthyl or it may not be protected. Preferred trifunctional amino acid protecting groups of the invention are tBu esters in the serine and threonine side chains; Boc in the lysine side chains, Trt in the cysteine side chains and Fmoc or Boc as a temporary protecting group of the N-terminal end.

Examples of these and other additional protecting groups, their introduction and their removal, are described in the literature [Greene T. W. and Wuts P. G. M., (1999) "Protective groups in organic synthesis" John Wiley & Sons, New York; Atherton B. and Sheppard R. C. (1989) "Solid Phase Peptide Synthesis: A practical approach" IRL Oxford University Press]. The term "protecting groups" also includes the polymer supports used in the solid phase synthesis.

When the synthesis is performed partially or entirely in solid phase, the polystyrene, polyethyleneglycol grafted in polystyrene supports and the like, can be mentioned as solid supports to be used in the process of the invention such as, by way of non-limiting example, p-methylbenzhydrylamine (MBHA) resins [Matsueda G. R. et al., Peptides 1981, 2, 45-50], 2-chlorotrityl resins [Barlos K. et al. 1989 Tetrahedron Lett. 30:3943-3946; Barlos K. et al., 1989 Tetrahedron Lett. 30, 3947-3951], TentaGel® resins (Rapp Polymere GmbH), ChemMatrix® resins (Matrix Innovation, Inc) and the like, which may or may not include a labile linker, such as 5-(4-aminomethyl-3,5-dimethoxyphenoxy)valeric acid (PAL) [Albericio F. et al., 1990, J. Org. Chem. 55, 3730-3743], the 2-[4-aminomethyl-(2,4-dimethoxyphenyl)]phenoxyacetic acid (AM) [Rink H., 1987, Tetrahedron Lett. 28, 3787-3790], Wang [Wang S. S., 1973, J. Am. Chem. Soc. 95, 1328-1333] and the like, which allow cleaving the semi-protected peptide and forming the cycle in solution with a step of deprotecting in solution or solid phase cycling and subsequently deprotecting and simultaneously cleaving the peptide.

Pharmaceutical Compositions

The compounds of the invention can be administered by any means which causes contacting the compounds with the action site thereof in the body of a mammal, preferably the body of a human, and in the form of a composition containing them.

In this sense, another aspect of the invention is a pharmaceutical composition comprising a pharmaceutically effective amount of at least one compound of general formula (I), their stereoisomers, mixtures thereof and/or their pharmaceutically acceptable salts, and at least one pharmaceutically acceptable excipient. The number and the nature of the pharmaceutically acceptable excipients depend on the desired dosage form. The pharmaceutically acceptable excipients are known by the person skilled in the art [Faulí i Trillo C. (1993) "Tratado de Farmacia Galénica", Luzán 5, S. A. Ediciones, Madrid]. Said compositions can be prepared by means of conventional methods known in the state of the art ["Remington: The Science and Practice of Pharmacy", 20th (2003) Genaro A. R., ed., Lippincott Williams & Wilkins, Philadelphia, US].

The pharmaceutical compositions containing the compounds of the invention, their stereoisomers, mixtures thereof and/or their pharmaceutically acceptable salts, can be administered through any suitable type of route, for example by topical, oral or parenteral route, for which purpose they will include the pharmaceutically acceptable excipients necessary for the formulation of the desired dosage form.

Uses

Another aspect of the present invention relates to the use of a compound of general formula (I), their stereoisomers, mixtures thereof and/or their pharmaceutically acceptable salts, in the preparation of a pharmaceutical composition for the treatment, prevention and/or diagnosis of those conditions, disorders and/or pathologies in which the sstr1, sstr2, sstr3, sstr4 and/or sstr5 somatostatin receptors are expressed.

In a more particular aspect, the present invention relates to the use of a compound of general formula (I), their stereoisomers, mixtures thereof and/or their pharmaceutically acceptable salts, in the preparation of a pharmaceutical composition for the treatment, prevention and/or diagnosis of those conditions, disorders and/or pathologies selected from the group consisting of acromegaly, symptomatic treatment of gastroenteropancreatic neuroendocrine tumors, diarrhea, cancer, tumors, neurodegenerative diseases, ocular diseases, immune system pathologies, inflammation, infections, esophageal varices, pain, wound healing, tissue regeneration, chronic pancreatitis, hypertrophic pulmonary osteoarthropathy and thyrotrophic adenoma.

In a more particular aspect, the present invention relates to the use of a compound of general formula (I), their stereoisomers, mixtures thereof and/or their pharmaceutically acceptable salts, in the preparation of a pharmaceutical composition for the treatment, prevention and/or diagnosis of those conditions, disorders and/or pathologies selected from the group consisting of acromegaly, inflammation, infections, esophageal varices, neuropathic pain, wound healing, tissue regeneration, chronic pancreatitis, hypertrophic pulmonary osteoarthropathy, thyrotrophic adenoma, grade 3-4 diarrhea, diarrhea associated with radiotherapy and/or chemotherapy treatment, symptomatic treatment of carcinoid syndrome or VIPomas, endocrine cancer, pancreatic cancer, colorectal cancer, breast cancer, ovarian cancer, prostate cancer, thyroid cancer, lung cancer, gastric cancer, hepatocellular carcinoma, Alzheimer's disease, arthritis, allergies, Lupus erythematosus, lymphoproliferative disorder, diabetic retinopathy, macular edema, Graves' ophthalmopathy, Cushing's syndrome, restenosis, angiogenesis, hyperthyroidism, hypothyroidism, hyperinsulinemia, psoriasis, hypercalcemia, Paget's disease, caquexia and Zollinger-Ellison syndrome.

DEFINITIONS

The abbreviations used in the present description have the following meanings:
Ac$_2$O, acetic anhydride; AcOH, acetic acid; Adpoc, 1-(1-adamantyl)-1-methylethoxy-carbonyl; All, allyl; Alloc, allyloxycarbonyl; Boc, tert-butoxycarbonyl; Bzl, benzyl; Cbz, benzyloxycarbonyl; cHx, cyclohexyl; ClZ, 2-chlorobenzyl; DCM, dichloromethane; Dde, N-[1-(4,4-dimethyl-2,6-dioxocyclohex-1-ylidene)ethyl]; DIEA, N,N'-diisopropylethylamine; DIPCDI, diisopropylcarbodiimide; Dmab, 4-(N-[1-(4,4-dimethyl-2,6-dioxocyclohexylidene)-3-methylbutyl]amino)benzyl; DMF, N,N-dimethylformamide; Dnp, 2,4-dinitrophenyl; DOTA, 1,4,7,10-tetraazacyclododecane-1,4,7,10-tetraacetic acid; DTPA, diethylenetriaminepentaacetic acid; ESI-MS, electrospray ionization mass spectrometry; Fm, fluorenylmethyl; Fmoc, 9-fluorenylmethoxycarbonyl; HF, hydrofluoric acid; HOBT, N-hydroxybenzotriazole; HPLC, High Performance Liquid Chromatography; IC$_{50}$, 50% maximal inhibitory concentration of a substance; ivDde, 1-(4,4-dimethyl-2,6-dioxo-cyclohexylidene)-3-methyl-butyl; Ki, inhibition constant of a drug; M, molecular mass; Mtt, methoxytrityl; μL, microliter; pmol, micromole; pNZ, para-nitrobenzyloxycarbonyl; RP-HPLC, reverse phase HPLC; SOM, somatostatin; tBu, tert-butyl; Teoc, 2-(trimethylsilyl)ethoxycarbonyl; TFA, trifluoroacetic acid; TFE, 2,2,2-trifluoroethanol; Tris, tris(hydroxymethyl)aminomethane; rt, retention time; Trt, trityl; Troc, 2,2,2-trichloroethoxycarbonyl; Z, benzyloxycarbonyl;

Amino Acids:
Ala (A): Alanine
Asn (N): Asparagine
Cys (C): Cysteine
Gly (G): Glycine
Lys (K): Lysine
Lys(Ac): (N-acetyl)lysine
Lys(Alloc): (N-allyloxycarbonyl)lysine
Lys(2-Cl-Z): (N-2-chlorobenzyl)lysine
Lys(Dde): (N-1-(4,4-dimethyl-2,6-dioxocyclohex-1-ylidene)ethyl)lysine
Lys(For): (N-formyl)lysine
Lys(isopropyl): (N-isopropyl)lysine
Lys(palmitoyl): (N-palmitoyl)lysine
Lys(Tfa): (N-trifluoroacetyl) lysine
Lys(Z): (N-Benzyloxycarbonyl) lysine
Phe (F): Phenylalanine
Ser (S): Serine
Thr (T): Threonine
Trp (W): Tryptophan
Msa: 2,4,6-trimethylphenylalanine or 3-mesityl-alanine
Msg: 2,4,6-trimethyl-phenylglycine or 2-mesityl-glycine
Qla: 3-(3'-quinolyl)alanine or β-(quinol-3-yl)-alanine

EXAMPLES

The following specific examples provided in this patent document serve to illustrate the nature of the present invention. These examples are included only for illustrative purposes and must not be interpreted as being limitations to the invention claimed herein.

Example 1

Synthesis of Compound 1

H-L-Ala-L-Gly-L-Cys-L-Lys-L-Asn-D-Msg-L-Phe-L-Trp-L-Lys-L-Thr-L-Phe-L-Thr-L-Ser-L-Cys-OH

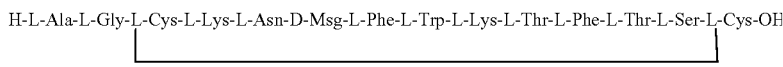

The resin was deposited in the synthesis reactor equipped with a filtering plate and a cock. The C-terminal residue was incorporated to 0.3 g 2-chlorotrityl resin (1.6 mmol/g). The first amino acid Fmoc-Cys(Trt)-OH (1 eq.) was dissolved in 3 mL DCM and 0.15 mL DMF. DIEA (3 eq.) was added. The solution with amino acid and base was transferred to the reactor and stirred for 45 min. After this time 0.24 mL MeOH were added and left to react for 10 min. The filtrate was filtered out and discarded. The resin was washed with DCM and DMF. The filtrates were filtered out and discarded in each washing. 2.5 eq. Fmoc-amino acid, 2.5 eq. HOBT and 2.5 eq. DIPCDI were used for the incorporation of the next amino acids. For the coupling reaction, it was left to react 40-60 min and the incorporation of the amino acid was controlled with a ninhydrin test. If the ninhydrin test was positive, a reactivation step was performed for 15-30 min with 0.83 eq. HOBT and 0.83 eq. DIPCDI. If the ninhydrin test continued to be positive, a recoupling was performed with 1.25 eq. Fmoc-amino acid, HOBT and DIPCDI. If the ninhydrin test was negative, the synthesis continued with the step of deprotecting the Fmoc group by means of treating with a solution of 20% piperidine in DMF twice. The peptidyl-resin was washed 5 times with DMF, filtering out and discarding the filtrates each time, and the next amino acid was then incorporated. 1.4 g peptidyl-resin were obtained.

1.4 g (0.43 mmol) peptidyl-resin were deposited in a reactor. 13.76 mL of an AcOH:TFE:DCM solution were added under magnetic stirring and left to react for 2 h. It was filtered in a reactor with a filter plate and the filtrate was recovered.

The resin was washed 3 times with 3.66 mL of the AcOH:TFE:DCM solution, the filtrates being recovered.

A solution of 1.12 g (10 eq.) iodine in 5.5 mL of AcOH:TFE:DCM solution was prepared. The filtrates recovered in acidolysis were transferred to the reactor that contained the iodine solution and the reaction was left under stirring. A solution of 2.34 g (22 eq.) sodium thiosulfate in 9.44 mL water was prepared and were added to the reactor once oxidation ended, complete discoloring being observed in 5 min. The stirring was stopped and the mixture was left to decant until phase separation. An extraction was performed by treating the aqueous phase 3 times with DCM and the organic phase 3 times with 5% citric acid:NaCl (v:w). The organic fractions were evaporated and the residue was vacuum dried. The solid residue was washed with water in a filter plate. 0.89 g of oxidized and protected product were obtained.

18.94 mL of the TFA:H$_2$O:DCM:anisole (55:5:30:10) reaction mixture were introduced in the reactor. 0.88 g of the semi-protected peptide were added to the previous solution and it was left to react for 4 h. Heptane (20.1 mL) was added and it was stirred for 5 min. The stirring was stopped and it was left to decant. The aqueous phase was poured on cold ether and was left to stand for 15-30 min. The obtained suspension was filtered through a filter plate and the filtrates were discarded. The residue was washed with ether, discarding the filtrates in each washing. The solid was freeze dried, obtaining 0.63 g of crude product.

The crude product was purified in a semi-preparative system equipped with an NW50 column packed with 10 micron kromasil silica. The peptide was suspended in 0.1N AcOH and DOWEX resin conditioned in 0.1N AcOH was added.

The final acetate compound was recovered by filtration and was characterized by mass spectrometry in ESI-MS equipment.

Characterization:

ESI-MS: Theoretical M=1664.7 g/mol, Experimental M: (m/z): [M+2H]$^+$/2=833.8

Analytical RP-HPLC: Gradient: 25-60% B in 20 min, rt=14.08 min; Isocratic: 33% B in 30 min, rt=11.2 min (B=0.07% TFA in acetonitrile).

Example 2

Synthesis of Compound 2

H-L-Ala-L-Gly-L-Cys-L-Lys-L-Asn-L-Phe-D-Msg-L-Trp-L-Lys-L-Thr-L-Phe-L-Thr-L-Ser-L-Cys-OH
|_____|

The compound was prepared as described in Example 1. 0.3 g of resin were used to start and 0.54 g of crude product were obtained with the same equivalent ratios.

Characterization:

ESI-MS: Theoretical M=1664.7 g/mol, Experimental M: (m/z): [M+2H]$^+$/2=833.8

Analytical RP-HPLC: Gradient: 25-60% B in 20 min, rt=14.3 min; Isocratic: 33% B in 30 min, rt=12.5 min (B=0.07% TFA in acetonitrile).

Example 3

Synthesis of Compound 3

H-L-Ala-L-Gly-L-Cys-L-Lys-L-Asn-L-Phe-L-Phe-L-Trp-L-Lys-L-Thr-D-Msg-L-Thr-L-Ser-L-Cys-OH
|_____|

The compound was prepared as described in Example 1. 0.3 g of peptidyl-resin were used to start and 0.39 g of crude product were obtained with the same equivalent ratios.

Characterization:

ESI-MS: Theoretical M=1664.7 g/mol, Experimental M: (m/z): [M+2H]$^+$/2=834.4

Analytical RP-HPLC: Gradient: 25-60% B in 20 min, rt=12.42 min; Isocratic: 29.5% B in 30 min, rt=13.3 min (B=0.07% TFA in acetonitrile).

Example 4

Synthesis of Compound 4

H-L-Ala-L-Gly-L-Cys-L-Lys-L-Asn-L-Msg-L-Phe-L-Trp-L-Lys-L-Thr-L-Phe-L-Thr-L-Ser-L-Cys-OH
|_____|

The compound was prepared as described in Example 1. 0.3 g of resin were used to start and 0.6 g of crude product were obtained with the same equivalent ratios.

Characterization:

ESI-MS: Theoretical M=1664.7 g/mol, Experimental M: (m/z): [M+2H]$^+$/2=834.1

Analytical RP-HPLC: Gradient: 25-60% B in 20 min, rt=12.5 min; Isocratic: 29.5% B in 30 min, rt=13.2 min (B=0.07% TFA in acetonitrile).

Example 5

Synthesis of Compound 5

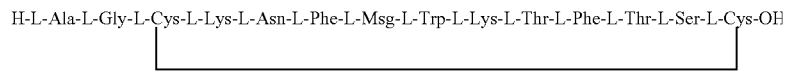

The compound was prepared as described in Example 1. 0.3 g of resin were used to start and 0.49 g of crude product were obtained with the same equivalent ratios.

Characterization:

ESI-MS: Theoretical M=1664.7 g/mol, Experimental M: (m/z): $[M+2H]^+/2=833.8$

Analytical RP-HPLC: Gradient: 25-60% B in 20 min, rt=12.3 min; Isocratic: 29.5% B in 30 min, rt=12.3 min (B=0.07% TFA in acetonitrile).

Example 6

Synthesis of Compound 6

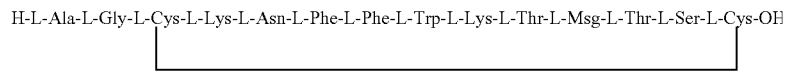

The compound was prepared as described in Example 1. 0.3 g of resin were used to start and 0.5 g of crude product were obtained with the same equivalent ratios.

Characterization:

ESI-MS: Theoretical M=1664.3 g/mol, Experimental M: (m/z): $[M+2H]^+/2=833.5$

Analytical RP-HPLC: Gradient: 25-60% B in 20 min, rt=12.1 min; Isocratic: 29.5% B in 30 min, rt=11.45 min (B=0.07% TFA in acetonitrile).

Example 7

Synthesis of Compound 7

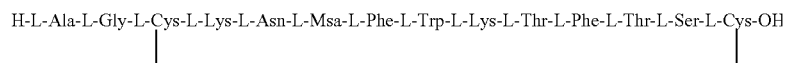

The compound was prepared as described in Example 1. 0.14 g of resin were used to start and 0.21 g of crude product were obtained with the same equivalent ratios.

Characterization:

ESI-MS: Theoretical M=1678.7 g/mol, Experimental M: (m/z): $[M+2H]^+/2=841.1$

Analytical RP-HPLC: Gradient: 25-60% B in 20 min, rt=14.3 min; Isocratic: 33% B in 30 min, rt=14.9 min (B=0.07% TFA in acetonitrile).

Example 8

Synthesis of Compound 8

H-L-Ala-L-Gly-L-Cys-L-Lys-L-Asn-L-Phe-L-Msa-L-Trp-L-Lys-L-Thr-L-Phe-L-Thr-L-Ser-L-Cys-OH
(cyclized between the two Cys residues)

The compound was prepared as described in Example 1. 0.14 g of resin were used to start and 0.23 g of crude product were obtained with the same equivalent ratios.

Characterization:

ESI-MS: Theoretical M=1678.7 g/mol, Experimental M: (m/z): $[M+2H]^+/2=840.9$

Analytical RP-HPLC: Gradient: 25-60% B in 20 min, rt=14.8 min; Isocratic: 35% B in 30 min, rt=11.08 min (B=0.07% TFA in acetonitrile).

Example 9

Synthesis of Compound 9

H-L-Ala-L-Gly-L-Cys-L-Lys-L-Asn-L-Phe-L-Phe-L-Trp-L-Lys-L-Thr-L-Msa-L-Thr-L-Ser-L-Cys-OH
(cyclized between the two Cys residues)

The compound was prepared as described in Example 1. 0.14 g of resin were used to start and 0.28 g of crude product were obtained with the same equivalent ratios.

Characterization:

ESI-MS: Theoretical M=1678.7 g/mol, Experimental M: (m/z): $[M+2H]^+/2=841$

Analytical RP-HPLC: Gradient: 25-60% B in 20 min, rt=14.1 min; Isocratic: 33% B in 30 min, rt=12.9 min (B=0.07% TFA in acetonitrile).

Example 10

Synthesis of Compound 10

H-L-Ala-L-Gly-L-Cys-L-Lys-L-Asn-D-Msa-L-Phe-L-Trp-L-Lys-L-Thr-L-Phe-L-Thr-L-Ser-L-Cys-OH
(cyclized between the two Cys residues)

The compound was prepared as described in Example 1. 0.25 g of resin were used to start and 0.39 g of crude product were obtained with the same equivalent ratios.
Characterization:
ESI-MS: Theoretical M=1678.7 g/mol, Experimental M: (m/z): [M+2H]$^+$/2=840.7
Analytical RP-HPLC: Gradient: 25-60% B in 20 min, rt=14.8 min; Isocratic: 33% B in 30 min, rt=17.7 min (B=0.07% TFA in acetonitrile).

Example 11

Synthesis of Compound 11

The compound was prepared as described in Example 1. 0.25 g of resin were used to start and 0.47 g of crude product were obtained with the same equivalent ratios.
Characterization:
ESI-MS: Theoretical M=1678.7 g/mol, Experimental M: (m/z): [M+2H]$^+$/2=840.7
Analytical RP-HPLC: Gradient: 25-60% B in 20 min, rt=15.7 min; Isocratic: 36% B in 30 min, rt=12.3 min (B=0.07% TFA in acetonitrile).

Example 12

Synthesis of Compound 12

The compound was prepared as described in Example 1. 0.25 g of resin were used to start and 0.46 g of crude product were obtained with the same equivalent ratios.
Characterization:
ESI-MS: Theoretical M=1678.7 g/mol, Experimental M: (m/z): [M+2H]$^+$/2=840.8
Analytical RP-HPLC: Gradient: 25-60% B in 20 min, rt=13.4 min; Isocratic: 32% B in 30 min, rt=12.03 min (B=0.07% TFA in acetonitrile).

Example 13

Synthesis of Compound 13

The compound was prepared as described in Example 1. 0.5 g of resin were used to start and 0.99 g of crude product were obtained with the same equivalent ratios.

Characterization:

ESI-MS: Theoretical M=1679.05 g/mol, Experimental M: (m/z): [M+2H]$^+$/2=840.8

Analytical RP-HPLC: Gradient: 25-60% B in 20 min, rt=12.2 min; Isocratic: 31% B in 30 min, rt=11.2 min (B=0.07% TFA in acetonitrile).

Example 14

Synthesis of Compound 14

H-L-Ala-L-Gly-L-Cys-L-Lys(Z)-L-Asn-L-Phe-L-Phe-L-Trp-L-Lys-L-Thr-L-Phe-L-Thr-L-Ser-L-Cys-OH

The compound was prepared as described in Example 1. 0.5 g of resin were used to start and 0.97 g of crude product were obtained with the same equivalent ratios.

Characterization:

ESI-MS: Theoretical M=1771.7 g/mol, Experimental M: (m/z): [M+2H]$^+$/2=887.3

Analytical RP-HPLC: Gradient: 25-60% B in 20 min, rt=15.9 min; Isocratic: 36% B in 30 min, rt=14.6 min (B=0.07% TFA in acetonitrile).

Example 15

Synthesis of Compound 15

H-L-Ala-L-Gly-L-Cys-L-Lys(Tfa)-L-Asn-L-Phe-L-Phe-L-Trp-L-Lys-L-Thr-L-Phe-L-Thr-L-Ser-L-Cys-OH

The compound was prepared as described in Example 1. 0.5 g of resin were used to start and 1 g of crude product was obtained with the same equivalent ratios.

Characterization:

ESI-MS: Theoretical M=1733.6 g/mol, Experimental M: (m/z): [M+2H]$^+$/2=867.6

Analytical RP-HPLC: Gradient: 25-60% B in 20 min, rt=14.4 min; Isocratic: 33% B in 30 min, rt=15.4 min (B=0.07% TFA in acetonitrile).

Example 16

Synthesis of Compound 16

H-L-Ala-L-Gly-L-Cys-L-Lys(2-Cl-Z)-L-Asn-L-Phe-L-Phe-L-Trp-L-Lys-L-Thr-L-Phe-L-Thr-L-Ser-L-Cys-OH

The compound was prepared as described in Example 1. 0.5 g of resin were used to start and 1.03 g of crude product were obtained with the same equivalent ratios.
Characterization:
ESI-MS: Theoretical M=1806.5 g/mol, Experimental M: (m/z): $[M+2H]^+/2=903.8$
Analytical RP-HPLC: Gradient: 25-60% B in 20 min, rt=16.7 min; Isocratic: 38% B in 30 min, rt=12.4 min (B=0.07% TFA in acetonitrile).

Example 17

Synthesis of Compound 17

H-L-Ala-L-Gly-L-Cys-L-Lys(For)-L-Asn-L-Phe-L-Phe-L-Trp-L-Lys-L-Thr-L-Phe-L-Thr-L-Ser-L-Cys-OH

The compound was prepared as described in Example 1. 0.5 g of resin were used to start and 0.89 g of crude product were obtained with the same equivalent ratios.
Characterization:
ESI-MS: Theoretical M=1665.67 g/mol, Experimental M: (m/z): $[M+2H]^+/2=833.7$
Analytical RP-HPLC: Gradient: 25-60% B in 20 min, rt=12.4 min; Isocratic: 31% B in 30 min, rt=10.5 min (B=0.07% TFA in acetonitrile).

Example 18

Synthesis of Compound 18

H-L-Ala-L-Gly-L-Cys-L-Lys(isopropyl)-L-Asn-L-Phe-L-Phe-L-Trp-L-Lys-L-Thr-L-Phe-L-Thr-L-Ser-L-Cys-OH The compound was prepared as described in Example 1. 0.5 g of resin were used to start and 1.05 g of crude product were obtained with the same equivalent ratios.
Characterization:
ESI-MS: Theoretical M=1679.2 g/mol, Experimental M: (m/z): $[M+2H]^+/2=840.7$
Analytical RP-HPLC: Gradient: 25-60% B in 20 min, rt=11.75 min; Isocratic: 29% B in 30 min, rt=13.7 min (B=0.07% TFA in acetonitrile).

Example 19

Synthesis of Compound 19

H-L-Ala-L-Gly-L-Cys-L-Lys(Alloc)-L-Asn-L-Phe-L-Phe-L-Trp-L-Lys-L-Thr-L-Phe-L-Thr-L-Ser-L-Cys-OH The compound was prepared as described in Example 1. 0.5 g of resin were used to start and 0.95 g of crude product were obtained with the same equivalent ratios.
Characterization:
ESI-MS: Theoretical M=1721.09 g/mol, Experimental M: (m/z): [M+2H]⁺/2=861.8
Analytical RP-HPLC: Gradient: 25-60% B in 20 min, rt=13.3 min; Isocratic: 34% B in 30 min, rt=12.1 min (B=0.07% TFA in acetonitrile).

Example 20

Synthesis of Compound 20

H-L-Ala-L-Gly-L-Cys-L-Lys(Dde)-L-Asn-L-Phe-L-Phe-L-Trp-L-Lys-L-Thr-L-Phe-L-Thr-L-Ser-L-Cys-OH

The compound was prepared as described in Example 1. 0.5 g of resin were used to start and 1.02 g of crude product were obtained with the same equivalent ratios.
Characterization:
ESI-MS: Theoretical M=1801.7 g/mol, Experimental M: (m/z): [M+2H]⁺/2=901.7
Analytical RP-HPLC: Gradient: 25-60% B in 20 min, rt=14.8 min; Isocratic: 34% B in 30 min, rt=13.5 min (B=0.07% TFA in acetonitrile).

Example 21

Synthesis of Compound 21

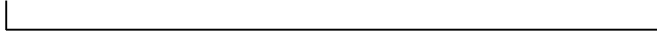

H-L-Ala-L-Gly-L-Cys-L-Lys(palmitoyl)-L-Asn-L-Phe-L-Phe-L-Trp-L-Lys-L-Thr-L-Phe-L-Thr-L-Ser-L-Cys-OH The compound was prepared as described in Example 1. 0.5 g of resin were used to start and 1.01 g of crude product were obtained with the same equivalent ratios.
Characterization:
ESI-MS: Theoretical M=1875.4 g/mol, Experimental M: (m/z): [M+2H]⁺/2=939.4
Analytical RP-HPLC: Gradient: 5-100% B in 20 min, rt=19.1 min; Isocratic: 55% B in 30 min, rt=13.8 min (B=0.07% TFA in acetonitrile).

Example 22

Synthesis of Compound 22

H-L-Ala-L-Gly-L-Cys-L-Lys-L-Asn-L-Phe-L-Phe-L-Qla-L-Lys-L-Thr-L-Phe-L-Thr-L-Ser-L-Cys-OH

The compound was prepared as described in Example 1. 0.3 g of resin were used to start and 0.58 g of crude product were obtained with the same equivalent ratios.
Characterization:
ESI-MS: Theoretical M=1649.9 g/mol, Experimental M: (m/z): [M+2H]⁺/2=825.6
Analytical RP-HPLC: Gradient: 25-60% B in 20 min, rt=8.3 min; Isocratic: 24% B in 30 min, rt=12.2 min (B=0.07% TFA in acetonitrile).

Example 23

Synthesis of Compound 23

H-L-Ala-L-Gly-L-Cys-L-Lys-L-Asn-L-Phe-L-Phe-D-Qla-L-Lys-L-Thr-L-Phe-L-Thr-L-Ser-L-Cys-OH
|_____|

The compound was prepared as described in Example 1. 0.3 g of resin were used to start and 0.63 g of crude product were obtained with the same equivalent ratios.
Characterization:
ESI-MS: Theoretical M=1649.9 g/mol, Experimental M: (m/z): $[M+2H]^+/2=825.6$
Analytical RP-HPLC: Gradient: 25-60% B in 20 min, rt=8.9 min; Isocratic: 25% B in 30 min, rt=11.1 min (B=0.07% TFA in acetonitrile).

Example 24

Synthesis of Compound 24

H-L-Ala-L-Gly-L-Cys-L-Lys-L-Asn-L-Msa-L-Phe-D-Trp-L-Lys-L-Thr-L-Phe-L-Thr-L-Ser-L-Cys-OH
|_____|

The compound was prepared as described in Example 1. 0.4 g of resin were used to start and 0.71 g of crude product were obtained with the same equivalent ratios.
Characterization:
ESI-MS: Theoretical M=1678.7 g/mol, Experimental M: (m/z): $[M+2H]^+/2=840.4$
Analytical RP-HPLC: Gradient: 25-60% B in 20 min, rt=16.1 min; Isocratic: 36% B in 30 min, rt=11.4 min (B=0.07% TFA in acetonitrile).

Example 25

Synthesis of Compound 25

H-L-Ala-L-Gly-L-Cys-L-Lys-L-Asn-L-Phe-L-Msa-D-Trp-L-Lys-L-Thr-L-Phe-L-Thr-L-Ser-L-Cys-OH
|_____|

The compound was prepared as described in Example 1. 0.4 g of resin were used to start and 0.66 g of crude product were obtained with the same equivalent ratios.
Characterization:
ESI-MS: Theoretical M=1678.7 g/mol, Experimental M: (m/z): $[M+2H]^+/2=840.6$
Analytical RP-HPLC: Gradient: 25-60% B in 20 min, rt=16.05 min; Isocratic: 36% B in 30 min, rt=11.3 min (B=0.07% TFA in acetonitrile).

Example 26

Synthesis of Compound 26

H-L-Ala-L-Gly-L-Cys-L-Lys-L-Asn-L-Phe-L-Phe-D-Trp-L-Lys-L-Thr-L-Msa-L-Thr-L-Ser-L-Cys-OH
|_____|

The compound was prepared as described in Example 1. 0.4 g of resin were used to start and 0.61 g of crude product were obtained with the same equivalent ratios.
Characterization:
ESI-MS: Theoretical M=1678.7 g/mol, Experimental M: (m/z): [M+2H]$^+$/2=840.5
Analytical RP-HPLC: Gradient: 25-60% B in 20 min, rt=15.6 min; Isocratic: 34% B in 30 min, rt=14.6 min (B=0.07% TFA in acetonitrile).

Example 27

Synthesis of Compound 27

The compound was prepared as described in Example 1. 0.1 g of resin were used to start and 0.12 g of crude product were obtained with the same equivalent ratios.
Characterization:
ESI-MS: Theoretical M=1721.1 g/mol, Experimental M: (m/z): [M+2H]$^+$/2=861.5
Analytical RP-HPLC: Gradient: 25-60% B in 20 min, rt=16.5 min; Isocratic: 37% B in 30 min, rt=16.6 min (B=0.07% TFA in acetonitrile).

Example 28

Synthesis of Compound 28

The compound was prepared as described in Example 1. 0.1 g of resin were used to start and 0.1 g of crude product were obtained with the same equivalent ratios.
Characterization:
ESI-MS: Theoretical M=1721.1 g/mol, Experimental M: (m/z): [M+2H]$^+$/2=861.4
Analytical RP-HPLC: Gradient: 25-60% B in 20 min, rt=15.38 min; Isocratic: 37% B in 30 min, rt=9.8 min (B=0.07% TFA in acetonitrile).

Example 29

Synthesis of Compound 29

The compound was prepared as described in Example 1. 0.1 g of resin were used to start and 0.12 g of crude product were obtained with the same equivalent ratios.
Characterization:
ESI-MS: Theoretical M=1721.1 g/mol, Experimental M: (m/z): [M+2H]$^+$/2=861.5
Analytical RP-HPLC: Gradient: 25-60% B in 20 min, rt=16.4 min; Isocratic: 37% B in 30 min, rt=15.4 min (B=0.07% TFA in acetonitrile).

Example 30

Synthesis of Compound 30

H-L-Ala-L-Gly-L-Cys-L-Lys-L-Asn-L-Msa-L-Msa-L-Trp-L-Lys-L-Thr-L-Msa-L-Thr-L-Ser-L-Cys-OH
|_____|

The compound was prepared as described in Example 1. 0.1 g of resin were used to start and 0.1 g of crude product were obtained with the same equivalent ratios.

Characterization:

ESI-MS: Theoretical M=1762.9 g/mol, Experimental M: (m/z): [M+2H]$^+$/2=882.6

Analytical RP-HPLC: Gradient: 25-60% B in 20 min, rt=18.3 min; Isocratic: 40% B in 30 min, rt=17.8 min (B=0.07% TFA in acetonitrile).

Example 31

Synthesis of Compound 31

H-L-Ala-L-Gly-L-Gly-L-Lys-L-Asn-L-Phe-L-Phe-L-Trp-L-Lys-L-Thr-L-Phe-L-Thr-L-Ser-L-Gly-NH2
|_____—CH$_2$—CH=CH—CH$_2$—_____|

The compound was synthesized following the general protocol described for the synthesis of the previous analogs starting from 1 g of Rink amide resin (0.45 mmol/g). The peptidyl-resin (200 mg, 0.09 mmol) was suspended in 1 mL DCM and 0.1 mL 0.4 M LiCl in DMF in a high pressure reactor. 15 mg (0.018 mmol) second generation Grubbs' catalyst were added and left to react for 1 h irradiating at 100° C. in a CEM Discovery microwave equipment. Once the metathesis reaction ended, the peptidyl-resin is passed to a reactor equipped with a filter plate and is washed with DMF, DCM, MeOH and ether. The peptidyl-resin was treated with a mixture of TFA:TIS:H$_2$O for 1 h and the compound was isolated by means of filtration. The filtrates were precipitated with ether. The obtained suspension was filtered through a filter plate and the filtrates were discarded. The residue was washed with ether, discarding the filtrates in each washing. The solid was freeze dried, obtaining 40 mg of crude product.

Characterization:

ESI-MS: Theoretical M=1597.8 g/mol, Experimental M: (m/z): [M+H$^+$]=1597.8

Analytical RP-HPLC: Gradient: 20-35% B in 6 min, rt=1.74 min (B=0.07% TFA in acetonitrile).

Example 32 sstr1, sstr2, sstr3, sstr4 and sstr 5 Receptor Binding Assay

The sstr1, sstr2, sstr3, sstr4 and sstr 5 receptor binding assay were performed using membranes from CHO-K1 cells (ATCC, American Type Culture Collection) in which the sstr1, sstr2, sstr3, sstr4 or sstr5 somatostatin receptors (Invitrogen plasmids) were selectively transfected. $^{125}$I-Tyr$^{11}$-somatostatin 14 was used as a radioactive ligand and somatostatin-14 as a cold ligand. The transfected cells were isolated by centrifugation and the pellet was resuspended in Tris buffer, and proteins were determined by the Bradford method. Dose-effect curves were elaborated to determine the IC$_{50}$ and Ki with those somatostatin analogs that displaced $^{125}$I-Tyr$^{11}$-somatostatin 14 to a concentration of 10 µM. Membranes from the clones expressed by the various receptors were incubated with a fixed concentration of tracer (0.1 nM) in the presence of increasing concentrations of somatostatin-14 and analogs, from 1 pM up to 1 µM. The mixture was incubated in 96-well plates for 1 h at 30° C., and after this time it was filtered in a Harvester to separate the bound radioactivity from the unbound radioactivity. The filter, which contained the membranes that had bound $^{125}$I-Tyr$^{11}$-somatostatin 14, was coated with of scintillation fluid and was counted in a MicroBeta counter. The radioactivity obtained in the absence of somatostatin-14 is considered as the total binding and the radioactivity obtained in the presence of 1 µM of somatostatin-14 is considered as the nonspecific binding. The specific binding is considered the difference between the total and nonspecific binding. The percentage of specific binding at each point was calculated. Tables 1-5 show the results of % specific binding of the somatostatin analogs to the 1-5 somatostatin receptors with respect to the somatostatin.

TABLE 1

Percentage of specific binding to the sstr1 receptor with respect to somatostatin.

| SSTR1 Concentration (M) | Compound 1 % specific binding | Compound 2 % specific binding | Compound 3 % specific binding | Compound 4 % specific binding | Compound 5 % specific binding | Compound 6 % specific binding |
|---|---|---|---|---|---|---|
| −13 | 100.0 | 100.0 | 100.0 | 100.0 | 100.0 | 100.0 |
| −12 | 94.0 | 102.7 | 98.4 | 100.5 | 119.9 | 100.0 |
| −11 | 100.1 | 92.0 | 97.1 | 92.5 | 109.7 | 87.1 |
| −10 | 100.9 | 95.1 | 94.6 | 99.7 | 114.9 | 89.2 |
| −9 | 95.7 | 92.9 | 96.2 | 89.6 | 127.1 | 97.5 |
| −8 | 94.2 | 83.4 | 86.8 | 91.2 | 111.9 | 99.3 |
| −7 | 74.5 | 64.3 | 76.3 | 76.4 | 87.6 | 65.2 |
| −6 | 40.5 | 22.0 | 20.0 | 27.4 | 25.0 | 13.0 |

| SSTR1 Concentration (M) | Compound 7 % specific binding | Compound 8 % specific binding | Compound 9 % specific binding | Compound 11 % specific binding | Compound 13 % specific binding | Compound 14 % specific binding |
|---|---|---|---|---|---|---|
| −13 | 100.0 | 100.0 | 100.0 | 100.0 | 100.0 | 100.0 |
| −12 | 101.6 | 105.2 | 107.9 | 95.8 | 94.2 | 77.0 |
| −11 | 99.0 | 85.5 | 94.8 | 90.0 | 88.1 | 79.2 |
| −10 | 101.1 | 82.0 | 88.7 | 83.8 | 88.5 | 79.2 |
| −9 | 76.1 | 67.7 | 89.8 | 72.6 | 70.5 | 66.4 |
| −8 | 41.8 | 38.9 | 55.8 | 68.0 | 42.0 | 43.2 |
| −7 | 19.2 | 18.0 | 25.6 | 29.6 | 12.5 | 18.0 |
| −6 | 4.6 | 0.6 | 11.1 | 5.2 | 1.7 | 1.2 |

| SSTR1 Concentration (M) | Compound 15 % specific binding | Compound 16 % specific binding | Compound 17 % specific binding | Compound 18 % specific binding | Compound 19 % specific binding | Compound 20 % specific binding |
|---|---|---|---|---|---|---|
| −13 | 100.0 | 100.0 | 100.0 | 100.0 | 100.0 | 100.0 |
| −12 | 87.2 | 97.5 | 104.1 | 89.2 | 93.7 | 95.3 |
| −11 | 92.6 | 100.9 | 101.3 | 81.2 | 90.5 | 99.9 |
| −10 | 93.6 | 92.4 | 99.4 | 76.8 | 94.1 | 95.5 |
| −9 | 86.7 | 89.9 | 88.2 | 53.2 | 77.0 | 86.9 |
| −8 | 46.1 | 79.2 | 52.4 | 22.7 | 40.9 | 47.6 |
| −7 | 23.1 | 38.4 | 29.5 | 1.3 | 19.3 | 20.1 |
| −6 | 9.1 | 13.9 | 17.2 | −2.8 | 4.5 | 6.6 |

| SSTR1 Concentration (M) | Compound 21 % specific binding | Compound 22 % specific binding | Compound 23 % specific binding | Compound 24 % specific binding | Compound 25 % specific binding | Compound 26 % specific binding |
|---|---|---|---|---|---|---|
| −13 | 100.0 | 100.0 | 100.0 | 100.0 | 100.0 | 100.0 |
| −12 | 94.1 | 101.1 | 98.2 | 101.3 | 100.8 | 106.9 |
| −11 | 102.0 | 103.7 | 107.9 | 96.7 | 97.9 | 98.2 |
| −10 | 88.6 | 87.4 | 99.0 | 94.3 | 80.1 | 97.7 |
| −9 | 78.8 | 67.8 | 89.0 | 78.2 | 53.5 | 81.1 |
| −8 | 70.4 | 41.8 | 64.8 | 50.8 | 42.2 | 54.8 |
| −7 | 40.0 | 26.9 | 31.8 | 35.2 | 31.8 | 42.1 |
| −6 | 20.1 | 18.1 | 10.1 | 23.8 | 25.1 | 24.7 |

| SSTR1 Concentration (M) | Compound 29 % specific binding | Compound 31 % specific binding |
|---|---|---|
| −13 | 100.0 | 100.0 |
| −12 | 104.0 | 96.0 |
| −11 | 103.9 | 91.5 |
| −10 | 91.7 | 75.6 |
| −9 | 91.4 | 48.6 |
| −8 | 86.2 | 33.6 |
| −7 | 57.1 | 30.4 |
| −6 | 14.0 | 16.9 |

TABLE 2

Percentage of specific binding to the sstr2 receptor with respect to somatostatin.

| SSTR2 Concentration (M) | Compound 1 % specific binding | Compound 2 % specific binding | Compound 3 % specific binding | Compound 4 % specific binding | Compound 5 % specific binding | Compound 6 % specific binding |
|---|---|---|---|---|---|---|
| −13 | 100.0 | 100.0 | 100.0 | 100.0 | 100.0 | 100.0 |
| −12 | 100.9 | 101.1 | 106.9 | 104.4 | 96.5 | 93.8 |

TABLE 2-continued

Percentage of specific binding to the sstr2 receptor with respect to somatostatin.

| | | | | | | |
|---|---|---|---|---|---|---|
| −11 | 97.4 | 96.4 | 100.6 | 106.0 | 101.7 | 98.1 |
| −10 | 97.0 | 95.2 | 99.5 | 104.7 | 101.3 | 97.7 |
| −9 | 98.3 | 96.0 | 99.0 | 104.4 | 101.7 | 98.1 |
| −8 | 88.9 | 82.7 | 97.0 | 97.4 | 97.7 | 94.3 |
| −7 | 62.8 | 49.8 | 72.7 | 64.4 | 55.9 | 72.1 |
| −6 | 12.1 | 10.0 | 13.3 | 6.5 | 8.4 | 17.2 |

| SSTR2 Concentration (M) | Compound 7 % specific binding | Compound 8 % specific binding | Compound 9 % specific binding | Compound 11 % specific binding | Compound 12 % specific binding | Compound 13 % specific binding |
|---|---|---|---|---|---|---|
| −13 | 100.0 | 100.0 | 100.0 | 100.0 | 100.0 | 100.0 |
| −12 | 96.9 | 66.6 | 72.8 | 99.2 | 99.0 | 100.6 |
| −11 | 93.9 | 57.4 | 61.2 | 93.4 | 95.9 | 90.1 |
| −10 | 83.7 | 43.0 | 50.1 | 92.6 | 90.9 | 68.1 |
| −9 | 60.7 | 23.1 | 24.8 | 78.9 | 82.2 | 30.3 |
| −8 | 33.7 | 9.9 | 6.6 | 33.9 | 42.9 | 9.8 |
| −7 | 23.0 | 3.7 | 2.0 | 5.5 | 9.8 | 4.0 |
| −6 | 11.1 | 1.8 | 2.3 | 0.5 | 2.4 | 1.3 |

| SSTR2 Concentration (M) | Compound 14 % specific binding | Compound 15 % specific binding | Compound 16 % specific binding | Compound 17 % specific binding | Compound 18 % specific binding | Compound 19 % specific binding |
|---|---|---|---|---|---|---|
| −13 | 100.0 | 100.0 | 100.0 | 100.0 | 100.0 | 100.0 |
| −12 | 52.9 | 70.9 | 69.1 | 104.8 | 78.2 | 47.9 |
| −11 | 46.5 | 53.6 | 64.2 | 88.0 | 59.8 | 35.4 |
| −10 | 39.5 | 39.3 | 57.8 | 59.6 | 41.8 | 20.1 |
| −9 | 24.2 | 19.3 | 42.3 | 28.6 | 15.1 | 10.9 |
| −8 | 9.0 | 5.8 | 14.8 | 10.6 | 6.0 | 3.5 |
| −7 | 3.3 | 1.5 | 4.9 | 3.1 | −0.2 | 1.7 |
| −6 | 1.1 | 0.5 | 2.0 | 1.1 | −2.0 | 1.0 |

| SSTR2 Concentration (M) | Compound 20 % specific binding | Compound 21 % specific binding | Compound 23 % specific binding | Compound 24 % specific binding | Compound 25 % specific binding | Compound 26 % specific binding |
|---|---|---|---|---|---|---|
| −13 | 100.0 | 100.0 | 100.0 | 100.0 | 100.0 | 100.0 |
| −12 | 60.3 | 88.1 | 103.3 | 100.7 | 68.4 | 91.1 |
| −11 | 53.6 | 90.3 | 100.8 | 98.0 | 40.0 | 84.3 |
| −10 | 44.1 | 81.3 | 91.0 | 96.1 | 18.8 | 68.4 |
| −9 | 22.3 | 56.7 | 68.3 | 79.9 | 6.1 | 27.0 |
| −8 | 8.0 | 22.6 | 35.6 | 52.7 | 4.6 | 7.1 |
| −7 | 2.9 | 7.6 | 14.3 | 17.6 | 3.3 | 3.3 |
| −6 | 2.3 | 3.6 | 4.7 | 3.7 | 0.6 | 1.4 |

| SSTR2 Concentration (M) | Compound 27 % specific binding | Compound 29 % specific binding | Compound 31 % specific binding |
|---|---|---|---|
| −13 | 100.0 | 100.0 | 100.0 |
| −12 | 98.0 | 98.6 | 98.0 |
| −11 | 96.7 | 93.9 | 87.4 |
| −10 | 95.9 | 86.9 | 71.6 |
| −9 | 94.7 | 71.3 | 50.8 |
| −8 | 73.5 | 24.3 | 19.4 |
| −7 | 22.5 | 4.7 | 9.2 |
| −6 | 2.2 | 1.6 | 4.6 |

TABLE 3

Percentage of specific binding to the sstr3 receptor with respect to somatostatin.

| SSTR3 Concentration (M) | Compound 6 % specific binding | Compound 7 % specific binding | Compound 9 % specific binding | Compound 10 % specific binding | Compound 13 % specific binding | Compound 14 % specific binding |
|---|---|---|---|---|---|---|
| −13 | 100.0 | 100.0 | 100.0 | 100.0 | 100.0 | 100.0 |
| −12 | 104.6 | 93.2 | 90.2 | 94.6 | 96.5 | 82.9 |
| −11 | 100.8 | 92.5 | 87.9 | 92.6 | 92.0 | 81.4 |
| −10 | 98.6 | 77.6 | 75.7 | 92.2 | 86.7 | 78.0 |
| −9 | 79.6 | 55.0 | 67.3 | 90.7 | 71.0 | 62.8 |
| −8 | 65.6 | 26.7 | 33.9 | 73.8 | 43.1 | 36.2 |

TABLE 3-continued

Percentage of specific binding to the sstr3 receptor with respect to somatostatin.

| | | | | | | |
|---|---|---|---|---|---|---|
| −7 | 41.3 | 9.9 | 14.5 | 30.4 | 14.5 | 8.3 |
| −6 | 10.0 | 1.6 | 5.3 | 4.8 | 3.4 | −1.1 |

| SSTR3 Concentration (M) | Compound 15 % specific binding | Compound 16 % specific binding | Compound 17 % specific binding | Compound 18 % specific binding | Compound 19 % specific binding | Compound 20 % specific binding |
|---|---|---|---|---|---|---|
| −13 | 100.0 | 100.0 | 100.0 | 100.8 | 100.0 | 100.0 |
| −12 | 93.3 | 99.1 | 100.1 | 91.8 | 92.4 | 94.9 |
| −11 | 87.7 | 92.8 | 96.9 | 84.8 | 82.2 | 87.7 |
| −10 | 82.4 | 88.4 | 89.3 | 65.0 | 70.7 | 81.7 |
| −9 | 65.6 | 76.5 | 79.9 | 31.8 | 64.5 | 62.8 |
| −8 | 36.5 | 45.2 | 42.5 | 9.8 | 30.7 | 31.7 |
| −7 | 11.8 | 14.6 | 14.8 | −0.3 | 5.9 | 5.3 |
| −6 | 4.6 | 3.8 | 3.8 | −1.7 | −1.0 | −3.2 |

| SSTR3 Concentration (M) | Compound 21 % specific binding | Compound 22 % specific binding | Compound 23 % specific binding | Compound 24 % specific binding | Compound 25 % specific binding | Compound 26 % specific binding |
|---|---|---|---|---|---|---|
| −13 | 100.0 | 100.0 | 100.0 | 100.0 | 100.0 | 100.0 |
| −12 | 100.7 | 87.6 | 87.9 | 82.3 | 93.2 | 79.6 |
| −11 | 101.4 | 83.4 | 82.1 | 70.2 | 87.3 | 73.7 |
| −10 | 95.8 | 75.5 | 65.2 | 63.5 | 81.7 | 67.0 |
| −9 | 82.7 | 56.8 | 34.7 | 40.8 | 74.6 | 47.1 |
| −8 | 56.6 | 26.3 | 9.4 | 11.0 | 48.9 | 14.3 |
| −7 | 23.0 | 3.2 | −0.3 | −0.2 | 21.3 | −1.4 |
| −6 | 4.8 | −5.3 | −5.3 | −3.8 | 4.3 | −6.7 |

| SSTR3 Concentration (M) | Compound 28 % specific binding | Compound 31 % specific binding |
|---|---|---|
| −13 | 100.0 | 100.0 |
| −12 | 96.5 | 94.5 |
| −11 | 92.3 | 86.3 |
| −10 | 88.2 | 83.5 |
| −9 | 86.4 | 71.1 |
| −8 | 58.5 | 40.9 |
| −7 | 19.6 | 13.6 |
| −6 | 1.5 | 2.2 |

TABLE 4

Percentage of specific binding to the sstr4 receptor with respect to somatostatin.

| SSTR4 Concentration (M) | Compound 3 % specific binding | Compound 6 % specific binding | Compound 7 % specific binding | Compound 8 % specific binding | Compound 9 % specific binding | Compound 13 % specific binding |
|---|---|---|---|---|---|---|
| −13 | 100.0 | 100.0 | 100.0 | 100.0 | 100.0 | 100.0 |
| −12 | 99.9 | 101.1 | 91.7 | 99.3 | 93.8 | 94.0 |
| −11 | 106.6 | 110.2 | 89.3 | 103.2 | 94.9 | 95.3 |
| −10 | 107.9 | 95.8 | 90.3 | 98.8 | 96.9 | 91.7 |
| −9 | 101.9 | 94.7 | 70.5 | 94.6 | 79.6 | 84.4 |
| −8 | 98.7 | 86.2 | 31.0 | 71.1 | 42.1 | 49.6 |
| −7 | 78.6 | 53.6 | 1.3 | 25.3 | 4.9 | 13.6 |
| −6 | 32.3 | 7.1 | −7.1 | −3.7 | −5.7 | 2.7 |

| SSTR4 Concentration (M) | Compound 14 % specific binding | Compound 15 % specific binding | Compound 16 % specific binding | Compound 17 % specific binding | Compound 18 % specific binding | Compound 19 % specific binding |
|---|---|---|---|---|---|---|
| −13 | 100.0 | 100.0 | 100.0 | 100.0 | 100.0 | 100.0 |
| −12 | 82.8 | 86.6 | 91.3 | 93.8 | 99.3 | 96.7 |
| −11 | 84.1 | 93.1 | 87.5 | 93.4 | 93.2 | 93.0 |
| −10 | 81.3 | 86.1 | 81.1 | 91.9 | 93.0 | 90.2 |
| −9 | 70.6 | 76.4 | 72.0 | 78.6 | 76.5 | 67.9 |
| −8 | 36.2 | 42.6 | 46.7 | 45.2 | 33.0 | 29.8 |

TABLE 4-continued

Percentage of specific binding to the sstr4 receptor with respect to somatostatin.

| | | | | | | |
|---|---|---|---|---|---|---|
| −7 | 13.5 | 14.0 | 15.2 | 12.7 | 7.8 | 9.3 |
| −6 | 1.8 | 2.2 | 4.1 | 4.1 | −0.4 | 1.1 |

| SSTR4 Concentration (M) | Compound 20 % specific binding | Compound 21 % specific binding | Compound 24 % specific binding | Compound 31 % specific binding |
|---|---|---|---|---|
| −13 | 100.0 | 100.0 | 100.0 | 100.0 |
| −12 | 93.3 | 101.3 | 99.9 | 90.1 |
| −11 | 94.9 | 94.0 | 95.2 | 94.3 |
| −10 | 90.0 | 90.7 | 91.7 | 87.0 |
| −9 | 81.3 | 62.7 | 76.1 | 65.0 |
| −8 | 51.3 | 32.8 | 41.3 | 27.9 |
| −7 | 11.1 | 15.2 | 17.0 | 16.4 |
| −6 | 2.4 | 7.5 | 3.5 | 7.7 |

TABLE 5

Percentage of specific binding to the sstr5 receptor with respect to somatostatin.

| SSTR5 Concentration (M) | Compound 6 % specific binding | Compound 7 % specific binding | Compound 9 % specific binding | Compound 13 % specific binding | Compound 14 % specific binding | Compound 15 % specific binding |
|---|---|---|---|---|---|---|
| −13 | 100.0 | 100.0 | 100.0 | 100.0 | 100.0 | 100.0 |
| −12 | 97.6 | 92.4 | 100.3 | 102.5 | 88.6 | 90.1 |
| −11 | 102.1 | 90.3 | 100.8 | 97.4 | 77.6 | 88.8 |
| −10 | 99.6 | 79.5 | 89.7 | 94.5 | 77.3 | 79.2 |
| −9 | 95.3 | 54.7 | 71.0 | 78.3 | 62.9 | 57.0 |
| −8 | 80.3 | 17.6 | 24.7 | 39.4 | 31.3 | 22.7 |
| −7 | 44.7 | 4.2 | 6.1 | 9.3 | 5.2 | 4.6 |
| −6 | 9.3 | −1.4 | 0.9 | −0.6 | −1.1 | −0.6 |

| SSTR5 Concentration (M) | Compound 16 % specific binding | Compound 17 % specific binding | Compound 18 % specific binding | Compound 19 % specific binding | Compound 20 % specific binding | Compound 21 % specific binding |
|---|---|---|---|---|---|---|
| −13 | 100.0 | 100.0 | 100.0 | 100.0 | 100.0 | 100.0 |
| −12 | 90.2 | 100.5 | 100.1 | 94.2 | 96.5 | 97.5 |
| −11 | 87.2 | 104.2 | 94.6 | 86.7 | 89.1 | 95.9 |
| −10 | 84.4 | 95.6 | 87.3 | 79.2 | 87.9 | 86.5 |
| −9 | 73.8 | 80.4 | 62.9 | 62.1 | 74.1 | 69.0 |
| −8 | 35.0 | 35.1 | 26.5 | 30.5 | 46.1 | 28.3 |
| −7 | 7.0 | 7.6 | 5.0 | 7.3 | 14.6 | 8.1 |
| −6 | −0.8 | −1.0 | −2.2 | 0.5 | 1.7 | 1.2 |

| SSTR5 Concentration (M) | Compound 23 % specific binding | Compound 24 % specific binding | Compound 25 % specific binding | Compound 26 % specific binding | Compound 28 % specific binding | Compound 31 % specific binding |
|---|---|---|---|---|---|---|
| −13 | 100.0 | 100.0 | 100.0 | 100.0 | 100.0 | 102.1 |
| −12 | 102.9 | 92.9 | 102.7 | 93.7 | 97.3 | 95.4 |
| −11 | 104.3 | 86.1 | 103.0 | 86.8 | 92.3 | 83.8 |
| −10 | 95.8 | 72.5 | 101.9 | 75.7 | 91.4 | 61.7 |
| −9 | 86.1 | 38.3 | 97.0 | 49.2 | 85.5 | 31.1 |
| −8 | 58.9 | 8.6 | 76.2 | 12.2 | 57.2 | 7.2 |
| −7 | 25.6 | 1.0 | 31.0 | 1.1 | 11.1 | −1.4 |
| −6 | 3.5 | −0.6 | 2.9 | −0.2 | 0.1 | −4.2 |

Example 33

Stability

The new compounds were incubated with 90% human serum at 37° C. Aliquots were extracted at different incubation times. Acetonitrile was added to precipitate the proteins from the serum, it was centrifuged and the supernatant was filtered and injected in the RP-HPLC (Grad: 20-80% B in 30 min, B=0.07% TFA in acetonitrile). The disappearance of the initial product was analyzed using the area corresponding to the initial product and the half-life time was calculated.

The new compounds have a half-life time greater than that of somatostatin. Compound 8 has a half-life time of 5.2 h. Compounds 10 and 11 have half-life times of 10.5 h and 8.1 h, respectively. Compound 21 has a half-life time of 41.7 h. Compounds 24, 25 and 26 have half-life times of 26.2, 24.6 and 41 h, respectively. Compound 27 has a half-life time of 43.9 h and compound 30 has a half-life time of 93.3 h.

Example 34

Synthesis of Compound 32

DOTA-L-Ala-L-Gyl-L-Cys-L-Lys-L-Asn-L-Msa-L-Phe-D-Trp-L-Lys-L-Thr-L-Phe-L-Thr-L-Ser-L-Cys-OH

The incorporation of the C-terminal residue was performed as described in Example 1 starting from 1 g of 2-chlorotrityl resin. The incorporation of the next 7 amino acids (fragment 7-14) was performed in an automatic synthesis reactor Liberty-CEM with an initial functionalization of 1.6 meq/g, scale 1 mM and 3 eq. Fmoc-amino acid, 3 eq. HOBT and 3 eq. DIPCDI. The incorporation of the last 6 amino acids was performed on 1.887 g of peptidyl-resin as described in Example 1, with the same ratio of equivalents. The incorporation of tri(tBu)-DOTA-OH was performed using 2.5 eq. tri(tBu)-DOTA-OH, 2.5 eq. benzotriazole-1-yl-oxytripyrrolidinophosphonium hexafluorophosphate, 2.5 eq. HOBt and 5 eq. DIEA in DMF during 60 min. The incorporation of DOTA was controlled with a ninhydrin test. 0.8454 g peptidyl-resin were obtained.

The subsequent oxidation and deprotection treatments were performed as described in Example 1 and 0.383 g of crude product were obtained.

The crude product was purified in a semi-preparative system equipped with an NW50 column packed with 10 micron kromasil silica, obtaining 0.103 g of purified product.

Characterization:

ESI-MS: Theoretical M=2065.7 g/mol, Experimental M: (m/z): $[M+2H]^+/2=1034.6$

Analytical RP-HPLC: Gradient: 25-60% B in 20 min, rt=13.1 min; Isocratic: 32% B in 30 min, rt=12.5 min (B=0.07% TFA in acetonitrile).

---

The invention claimed is:
1. A compound of general formula (I)

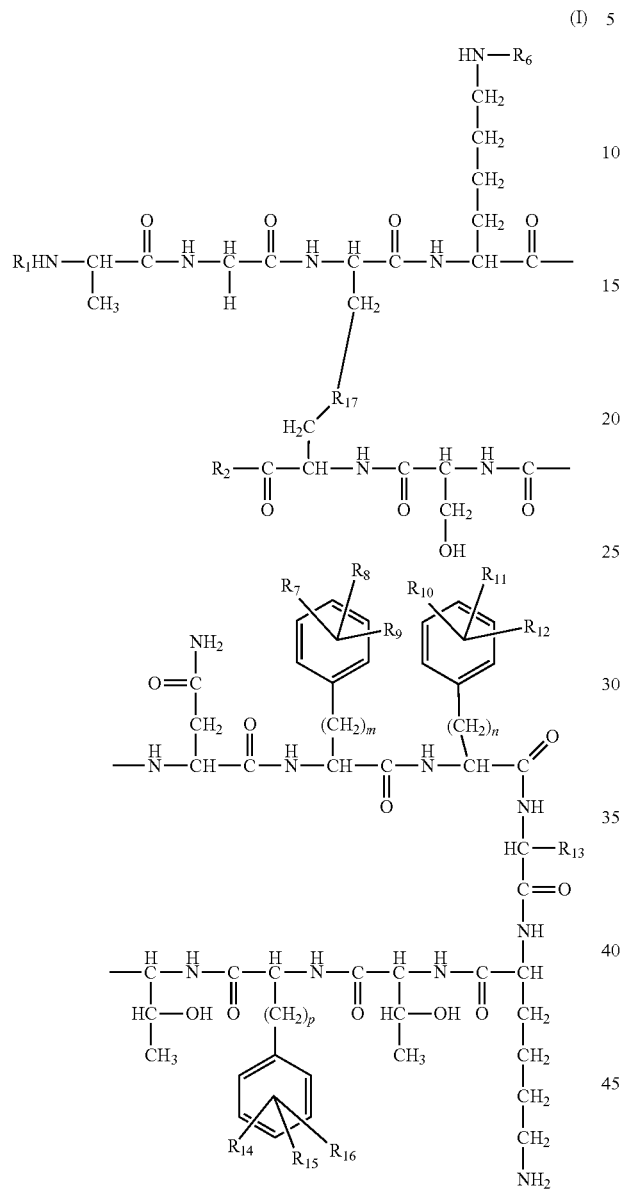

stereoisomers thereof, mixtures thereof or their pharmaceutically acceptable salts thereon, wherein:

$R_1$ is selected from the group consisting of H, a substituted or unsubstituted non-cyclic aliphatic group, a substituted or unsubstituted alicyclyl group, a substituted or unsubstituted heterocyclyl group, a substituted or unsubstituted heteroarylalkyl group, a substituted or unsubstituted aryl group, a substituted or unsubstituted aralkyl group, a polyethylene glycol polymer, a chelating agent and $R_5$—CO—;

$R_2$ is selected from the group consisting of —$NR_3R_4$, —$OR_3$ and —$SR_3$;

$R_6$ is selected from the group consisting of H, acetyl, trifluoroacetyl, isopropyl, palmitoyl, allyloxycarbonyl, 2-chlorobenzyl, formyl, N-[1-(4,4-dimethyl-2,6-dioxocyclohex-1-ylidene)ethyl] and benzyloxycarbonyl;

$R_7$, $R_8$, $R_9$, $R_{10}$, $R_{11}$, $R_{12}$, $R_{14}$, $R_{15}$ and $R_{16}$ are selected independently from one another from the group consisting of H and a non-cyclic aliphatic group;

m is an integer from 0 to 6 with the condition that when $R_7$, $R_8$ and $R_9$ are H, then m is different from 0;

n is an integer from 0 to 6 with the condition that when $R_{10}$, $R_{11}$ and $R_{12}$ are H, then n is different from 0;

p is an integer from 0 to 6 with the condition that when $R_{14}$, $R_{15}$ and $R_{16}$ are H, then p is different from 0;

$R_{13}$ is selected from the group consisting of L-(3-quinolyl)methyl, D-(3-quinolyl)methyl, L-(3-indolyl)methyl and D-(3-indolyl)methyl;

$R_{17}$ is —SS—;

$R_3$ and $R_4$ are independently selected from the group consisting of H, a substituted or unsubstituted non-cyclic aliphatic group, a substituted or unsubstituted alicyclyl group, a substituted or unsubstituted heterocyclyl group, a substituted or unsubstituted heteroarylalkyl group, a substituted or unsubstituted aryl group, a substituted or unsubstituted aralkyl group and a polymer;

$R_5$ is selected from the group consisting of H, a substituted or unsubstituted non-cyclic aliphatic group, a substituted or unsubstituted alicyclyl group, a substituted or unsubstituted aryl group, a substituted or unsubstituted aralkyl group, a substituted or unsubstituted heterocyclyl group and a substituted or unsubstituted heteroarylalkyl group; and with the condition that when $R_6$, $R_7$, $R_8$, $R_9$, $R_{10}$, $R_{11}$, $R_{12}$, $R_{14}$, $R_{15}$ and $R_{16}$ are all equal to H and n, m and p are equal to 1, $R_{13}$ is equal to L-(3-quinolyl)methyl or to D-(3-quinolyl)methyl.

2. The compound according to claim 1, wherein $R_1$ is selected from the group consisting of H, a polymer of general formula (II)

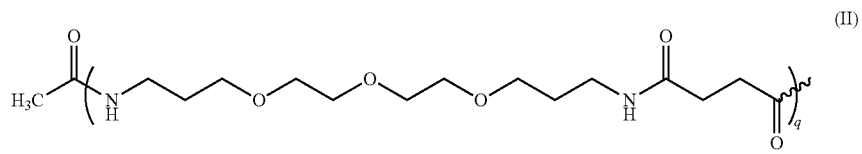

where q ranges from 1 to 5, and $R_5$—CO—, where $R_5$ is selected from the group consisting of substituted or unsubstituted $C_1$-$C_{24}$ alkyl radical, substituted or unsubstituted $C_2$-$C_{24}$ alkenyl radical, substituted or unsubstituted $C_2$-$C_{24}$ alkynyl radical, substituted or unsubstituted $C_3$-$C_{24}$ cycloalkyl radical, substituted or unsubstituted $C_5$-$C_{24}$ cycloalkenyl radical, substituted or unsubstituted $C_8$-$C_{24}$ cycloalkynyl radical, substituted or unsubstituted $C_6$-$C_{30}$ aryl radical, substituted or unsubstituted $C_7$-$C_{24}$ aralkyl radical, a substituted or unsubstituted heterocyclyl radical having 3-10 ring members, and a substituted or unsubstituted heteroarylalkyl radical having 2 to 24 carbon atoms and having 1 to 3 atoms other than carbon where the alkyl chain is of 1 to 6 carbon atoms.

3. The compound according to claim 2, wherein $R_1$ is selected from the group consisting of H, acetyl, tert-butanoyl, hexanoyl, 2-methylhexanoyl, cyclohexanecarboxyl, octanoyl, decanoyl, lauroyl, myristoyl, palmitoyl, stearoyl, behenyl, oleoyl and linoleoyl.

4. The compound according to claim 1, wherein $R_1$ is a chelating agent complexed with a detectable element or a radiotherapeutic element.

5. The compound according to claim 2, wherein $R_3$ and $R_4$ are independently selected from the group consisting of H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, a substituted or unsubstituted heterocyclyl having 3-10 ring members, and a substituted or unsubstituted heteroarylalkyl group having 2 to 24 carbon atoms and having 1 to 3 atoms other than carbon where the alkyl chain is of 1 to 6 carbon atoms, and a polymer of general formula (II) where q ranges from 1 to 5.

6. The compound according to claim 5, wherein $R_3$ and $R_4$ are selected from the group consisting of H, methyl, ethyl, hexyl, dodecyl and hexadecyl.

7. The compound according to claim 1, wherein $R_7$, $R_8$ and $R_9$ are equal to one another and are in an ortho-, para-, ortho-configuration or a meta-, para-, meta-configuration, $R_{10}$, $R_{11}$ and $R_{12}$ are equal to one another and are in an ortho-, para-, ortho-configuration or a meta-, para-, meta-configuration, and $R_{14}$, $R_{15}$ and $R_{16}$ are equal to one another and are in an ortho-, para-, ortho-configuration or a meta-, para-, meta-configuration.

8. The compound according to claim 2, wherein $R_1$ is selected from the group consisting of H, acetyl, lauroyl, myristoyl, palmitoyl or a polymer of general formula (II) where q ranges between 1 and 5, $R_2$ is —$NR_3R_4$ or —$OR_3$ where $R_3$ and $R_4$ are independently selected from the group consisting of H, methyl, ethyl, hexyl, dodecyl and hexadecyl, $R_6$ is H, $R_7$, $R_8$ and $R_9$ are methyl and are in an ortho-, para-, ortho-configuration or a meta-, para-, meta-configuration, m is 0 or 1, $R_{10}$, $R_{11}$, $R_{12}$, $R_{14}$, $R_{15}$ and $R_{16}$ are H, n and p are equal to 1, and $R_{13}$ is selected from the group consisting of L-(3-indolyl)methyl and D-(3-indolyl)methyl.

9. The compound according to claim 2, wherein $R_1$ is selected from the group consisting of H, acetyl, lauroyl, myristoyl, palmitoyl and a polymer of general formula (II) where q ranges between 1 and 5, $R_2$ is —$NR_3R_4$ or —$OR_3$ where $R_3$ and $R_4$ are independently selected from the group consisting of H, methyl, ethyl, hexyl, dodecyl and hexadecyl, $R_6$ is H, $R_{10}$, $R_{11}$ and $R_{12}$ are methyl and are in an ortho-, para-, ortho-configuration or a meta-, para-, meta-configuration, n is 0 or 1, $R_7$, $R_8$, $R_9$, $R_{14}$, $R_{15}$ and $R_{16}$ are H, m and p are equal to 1, $R_{13}$ is selected from the group consisting of L-(3-indolyl)methyl and D-(3-indolyl)methyl and $R_{17}$ is —S—S—.

10. The compound according to claim 2, wherein $R_1$ is selected from the group consisting of H, acetyl, lauroyl, myristoyl, palmitoyl and a polymer of general formula (II) where q ranges from 1 to 5, $R_2$ is —$NR_3R_4$ or —$OR_3$ where $R_3$ and $R_4$ are independently selected from the group consisting of H, methyl, ethyl, hexyl, dodecyl and hexadecyl, $R_6$ is H, $R_{14}$, $R_{15}$ and $R_{16}$ are methyl and are in an ortho-, para-, ortho-configuration or a meta-, para-, meta-configuration, p is 0 or 1, $R_7$, $R_8$, $R_9$, $R_{10}$, $R_{11}$ and $R_{12}$ are H, m and n are equal to 1, $R_{13}$ is selected from the group consisting of L-(3-indolyl)methyl and D-(3-indolyl)methyl and $R_{17}$ is —S—S—.

11. The compound according to claim 2, wherein $R_1$ is selected from the group consisting of H, acetyl, lauroyl, myristoyl, palmitoyl and a polymer of general formula (II) where q ranges between 1 and 5, $R_2$ is —$NR_3R_4$ or —$OR_3$ where $R_3$ and $R_4$ are independently selected from the group consisting of H, methyl, ethyl, hexyl, dodecyl and hexadecyl, $R_6$ is H, $R_7$, $R_8$, $R_9$, $R_{10}$, $R_{11}$ and $R_{12}$ are methyl and are in an ortho-, para-, ortho-configuration or a meta-, para-, meta-configuration, m and n are 0 or 1, $R_{14}$, $R_{15}$ and $R_{16}$ are H, p is equal to 1, $R_{13}$ is selected from the group consisting of L-(3-indolyl)methyl and D-(3-indolyl)methyl and $R_{17}$ is —S—S—.

12. The compound according to claim 2, wherein $R_1$ is selected from the group consisting of H, acetyl, lauroyl, myristoyl, palmitoyl and a olyrner of general formula (II) where q ranges between 1 and 5, $R_2$ is —$NR_3R_4$ or —$OR_3$ where $R_3$ and $R_4$ are independently selected from the group consisting of H, methyl, ethyl, hexyl, dodecyl and hexadecyl, $R_6$ is H, $R_7$, $R_8$, $R_9$, $R_{14}$, $R_{15}$ and $R_{16}$ are methyl and are in an ortho-, para-, ortho-configuration or a meta-, para-, meta-configuration, m and p are 0 or 1, $R_{10}$, $R_{11}$ and $R_{12}$ are H, n is equal to 1, $R_{13}$ is selected from the group consisting of L-(3-indolyl)methyl and D-(3-indolyl)methyl and $R_{17}$ is —S—S—.

13. The compound according to claim 2, wherein $R_1$ is selected from the group consisting of H, acetyl, lauroyl, myristoyl, palmitoyl and a polymer of general formula (II) where q ranges between 1 and 5, $R_2$ is —$NR_3R_4$ or —$OR_3$ where $R_3$ and $R_4$ are independently selected from the group consisting of H, methyl, ethyl, hexyl, dodecyl and hexadecyl, $R_6$ is H, $R_{10}$, $R_{11}$, $R_{12}$, $R_{14}$, $R_{15}$ and $R_{16}$ are methyl and are in an ortho-, para-, ortho-configuration or a meta-, para-, meta-configuration, n and p are 0 or 1, $R_7$, $R_8$ and $R_9$ are H, m is equal to 1, $R_{13}$ is selected from the group consisting of L-(3-indolyl)methyl and D-(3-indolyl)methyl and $R_{17}$ is —S—S—.

14. The compound according to claim 2, wherein $R_1$ is selected from the group consisting of H, acetyl, lauroyl, myristoyl, palmitoyl and a polymer of general formula (II) where q ranges between 1 and 5, $R_2$ is —$NR_3R_4$ or —$OR_3$ where $R_3$ and $R_4$ are independently selected from the group consisting of H, methyl, ethyl, hexyl, dodecyl and hexadecyl, $R_6$ is selected from the group consisting of acetyl, palmitoyl, trifluoroacetyl, isopropyl, allyloxycarbonyl, 2-chlorobenzyl, N-[1-(4,4-dimethyl-2,6-dioxocyclohex-1-ylidene)ethyl], $R_7$, $R_8$, $R_9$, $R_{10}$, $R_{11}$, $R_{12}$, $R_{14}$, $R_{15}$ and $R_{16}$ are H, m, n and p are equal to 1, $R_{13}$ is selected from the group consisting of L-(3-quinolyl)methyl and D-(3-quinolyl)methyl and $R_{17}$ is —S—S—.

15. The compound according to claim 2, wherein $R_1$ is selected from the group consisting of H, acetyl, lauroyl, myristoyl, palmitoyl or a polymer and a polymer of general formula (II) where q ranges between 1 and 5, $R_2$ is —$NR_3R_4$ or —$OR_3$ where $R_3$ and $R_4$ are independently selected from the group consisting of H, methyl, ethyl, hexyl, dodecyl and hexadecyl, $R_6$ is H, $R_7$, $R_8$, $R_9$, $R_{10}$, $R_{11}$, $R_{12}$, $R_{14}$, $R_{15}$ and $R_{16}$ are H, m, n and p are equal to 1, $R_{13}$ is selected from the group consisting of L-(3-quinolyl)methyl and D-(3-quinolyl)methyl and $R_{17}$ is —S—S—.

16. A process for obtaining a compound of general formula (I), their stereoisomers, mixtures thereof, or their cosmetically or pharmaceutically acceptable salts as defined in claim 1, which is performed in solid phase or in solution.

17. The process according to claim 16, which includes the following steps:
1) performing solid phase synthesis;
2) cleaving the peptide from the polymer support;
3) cycling the peptide in solution; and
4) eliminating the protecting groups or alternatively
   a) performing solid phase synthesis;
   b) performing solid phase cycling; and
   c) cleaving the peptide from the polymer support and simultaneously eliminating the protecting groups.

18. A pharmaceutical composition comprising a pharmaceutically effective amount of at least one compound of general formula (I), their stereoisomers, mixtures thereof or their pharmaceutically acceptable salts, according to claim 1, and at least one pharmaceutically acceptable excipient.

19. A method of treatment of those conditions, disorders and/or pathologies in which sstr1, sstr2, sstr3, sstr4 and/or sstr5 somatostatin receptors are expressed which comprises administration of an effective amount of a compound according to claim 1.

20. The method according to claim 19, wherein the conditions, disorders and/or pathologies are selected from the group consisting of acromegaly, symptomatic treatment of gastroenteropancreatic neuroendocrine tumors, diarrhea, cancer, tumors, neurodegenerative diseases, ocular diseases, immune system pathologies, inflammation, infections, esophageal varices, pain, wound healing, tissue regeneration, chronic pancreatitis, hypertrophic pulmonary osteoarthropathy and thyrotrophic adenoma.

21. The method according to claim 19, wherein conditions, disorders and/or pathologies are selected from the group consisting of acromegaly, symptomatic treatment of gastroenteropancreatic neuroendocrine tumors, grade 3-4 diarrhea, diarrhea associated with radiotherapy and/or chemotherapy treatment, symptomatic treatment of carcinoid syndrome or VIPomas, endocrine cancer, pancreatic cancer, colorectal cancer, breast cancer, ovarian cancer, prostate cancer, thyroid cancer, lung cancer, gastric cancer, hepatocellular carcinoma, Alzheimer's disease, arthritis, allergies, Lupus erythematosus, lymphoproliferative disorder, diabetic retinopathy, macular edema, Graves' ophthalmopathy, Cushing's syndrome, neuropathic pain, restenosis, angiogenesis, hyperthyroidism, hypothyroidism, hyperinsulinemia, psoriasis, hypercalcemia, Paget's disease, caquexia and Zollinger-Ellison syndrome.

22. A compound of general formula (I)

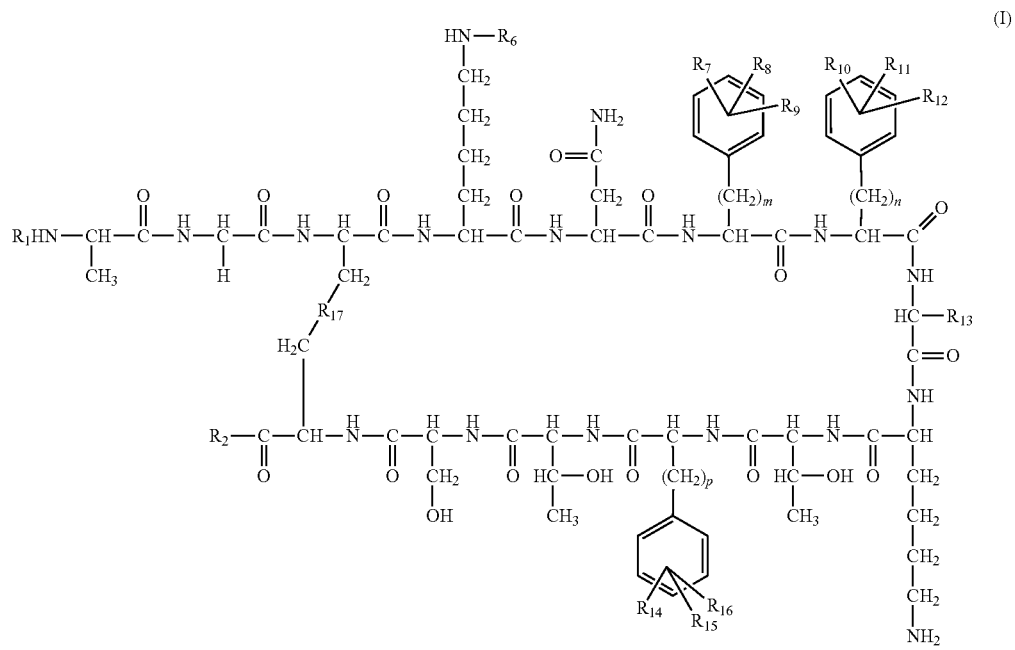

their stereoisomers, mixtures thereof or their pharmaceutically acceptable salts, wherein:

$R_1$ is H;
$R_2$ is —$OR_3$;
$R_3$ is H;
$R_6$ is H;
$R_7$, $R_8$, and $R_9$ are methyl and are in an ortho-, para-, or ortho-configuration;
$R_{10}$, $R_{11}$, $R_{12}$, $R_{14}$, $R_{15}$ and $R_{16}$ are H;
m is 1;
n is 1;
p is 1;
$R_{13}$ is D-(3-indolyl)methyl; and
$R_{17}$ is —SS—.

* * * * *

UNITED STATES PATENT AND TRADEMARK OFFICE
CERTIFICATE OF CORRECTION

Page 1 of 1

PATENT NO. : 8,946,154 B2
APPLICATION NO. : 13/319285
DATED : February 3, 2015
INVENTOR(S) : Antonio Parente Duena et al.

It is certified that error appears in the above-identified patent and that said Letters Patent is hereby corrected as shown below:

In the Claims

Column 66, Line 63, Claim 15:

After "myristoyl, palmitoyl"
Delete "or a polymer".

Signed and Sealed this
Sixteenth Day of June, 2015

Michelle K. Lee
*Director of the United States Patent and Trademark Office*

SEQUENCE LISTING

```
<160> NUMBER OF SEQ ID NOS: 32

<210> SEQ ID NO 1
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "D-2,4,6-trimethyl-phenylglycine"

<400> SEQUENCE: 1

Ala Gly Cys Lys Asn Xaa Phe Trp Lys Thr Phe Thr Ser Cys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (7)..(7)
<223> OTHER INFORMATION: /replace = "D-2,4,6-trimethyl-phenylglycine"

<400> SEQUENCE: 2

Ala Gly Cys Lys Asn Phe Xaa Trp Lys Thr Phe Thr Ser Cys
1               5                   10

<210> SEQ ID NO 3
<211> LENGTH: 14
<212> TYPE: PRT
<213> ORGANISM: Artificial Sequence
```

```
-continued

<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (11)..(11)
<223> OTHER INFORMATION: /replace = "D-2,4,6-trimethyl-phenylglycine"

<400> SEQUENCE: 3

Ala Gly Cys Lys Asn Phe Phe Trp Lys Thr Xaa Thr Ser Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "L-2,4,6-trimethyl-phenylglycine"

<400> SEQUENCE: 4

Ala Gly Cys Lys Asn Xaa Phe Trp Lys Thr Phe Thr Ser Cys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (7)..(7)
<223> OTHER INFORMATION: /replace = "L-2,4,6-trimethyl-phenylglycine"

<400> SEQUENCE: 5

Ala Gly Cys Lys Asn Phe Xaa Trp Lys Thr Phe Thr Ser Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (11)..(11)
<223> OTHER INFORMATION: /replace = "L-2,4,6-trimethyl-phenylglycine"

<400> SEQUENCE: 6

Ala Gly Cys Lys Asn Phe Phe Trp Lys Thr Xaa Thr Ser Cys
1               5                   10

<210> SEQ ID NO 7
<211> LENGTH: 14
<212> TYPE: PRT
```

```
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "L-2,4,6-trimethyl-phenylalanine"

<400> SEQUENCE: 7

Ala Gly Cys Lys Asn Xaa Phe Trp Lys Thr Phe Thr Ser Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (7)..(7)
<223> OTHER INFORMATION: /replace = "L-2,4,6-trimethyl-phenylalanine"

<400> SEQUENCE: 8

Ala Gly Cys Lys Asn Phe Xaa Trp Lys Thr Phe Thr Ser Cys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (11)..(11)
<223> OTHER INFORMATION: /replace = "L-2,4,6-trimethyl-phenylalanine"

<400> SEQUENCE: 9

Ala Gly Cys Lys Asn Phe Phe Trp Lys Thr Xaa Thr Ser Cys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "D-2,4,6-trimethyl-phenylalanine"

<400> SEQUENCE: 10

Ala Gly Cys Lys Asn Xaa Phe Trp Lys Thr Phe Thr Ser Cys
1               5                   10

<210> SEQ ID NO 11
<211> LENGTH: 14
```

```
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (7)..(7)
<223> OTHER INFORMATION: /replace = "D-2,4,6-trimethyl-phenylalanine"

<400> SEQUENCE: 11

Ala Gly Cys Lys Asn Phe Xaa Trp Lys Thr Phe Thr Ser Cys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (11)..(11)
<223> OTHER INFORMATION: /replace = "D-2,4,6-trimethyl-phenylalanine"

<400> SEQUENCE: 12

Ala Gly Cys Lys Asn Phe Phe Trp Lys Thr Xaa Thr Ser Cys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: MOD_RES
<222> LOCATION: (4)..(4)
<223> OTHER INFORMATION: ACETYLATION

<400> SEQUENCE: 13

Ala Gly Cys Lys Asn Phe Phe Trp Lys Thr Phe Thr Ser Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (4)..(4)
<223> OTHER INFORMATION: /replace = "(N-benzyloxycarbonyl)lysine"

<400> SEQUENCE: 14

Ala Gly Cys Xaa Asn Phe Phe Trp Lys Thr Phe Thr Ser Cys
1               5                   10

<210> SEQ ID NO 15
```

```
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (4)..(4)
<223> OTHER INFORMATION: /replace = "(N-trifluoroacetyl)lysine"

<400> SEQUENCE: 15

Ala Gly Cys Xaa Asn Phe Phe Trp Lys Thr Phe Thr Ser Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (4)..(4)
<223> OTHER INFORMATION: /replace = "(N-2-chlorobenzyl)lysine"

<400> SEQUENCE: 16

Ala Gly Cys Xaa Asn Phe Phe Trp Lys Thr Phe Thr Ser Cys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (4)..(4)
<223> OTHER INFORMATION: /replace = "(N-formyl)lysine"

<400> SEQUENCE: 17

Ala Gly Cys Xaa Asn Phe Phe Trp Lys Thr Phe Thr Ser Cys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (4)..(4)
<223> OTHER INFORMATION: /replace = "(N-isopropyl)lysine"

<400> SEQUENCE: 18

Ala Gly Cys Xaa Asn Phe Phe Trp Lys Thr Phe Thr Ser Cys
1               5                   10
```

-continued

```
<210> SEQ ID NO 19
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (4)..(4)
<223> OTHER INFORMATION: /replace = "(N-allyloxycarbonyl)lysine"

<400> SEQUENCE: 19

Ala Gly Cys Xaa Asn Phe Phe Trp Lys Thr Phe Thr Ser Cys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (4)..(4)
<223> OTHER INFORMATION: /replace = "(N-1-(4,4-dimethyl-2,6-
      dioxocyclohex-1-ylidene)ethyl)lysine"

<400> SEQUENCE: 20

Ala Gly Cys Xaa Asn Phe Phe Trp Lys Thr Phe Thr Ser Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (4)..(4)
<223> OTHER INFORMATION: /replace = "(N-palmitoyl)lysine"

<400> SEQUENCE: 21

Ala Gly Cys Xaa Asn Phe Phe Trp Lys Thr Phe Thr Ser Cys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (8)..(8)
<223> OTHER INFORMATION: /replace = "L-3-(3'-quinolyl)alanine"

<400> SEQUENCE: 22

Ala Gly Cys Lys Asn Phe Phe Xaa Lys Thr Phe Thr Ser Cys
1               5                   10
```

<210> SEQ ID NO 23
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (8)..(8)
<223> OTHER INFORMATION: /replace = "D-3-(3'-quinolyl)alanine"

<400> SEQUENCE: 23

Ala Gly Cys Lys Asn Phe Phe Xaa Lys Thr Phe Thr Ser Cys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "2,4,6-trimethyl-phenylalanine"
<220> FEATURE:
<221> NAME/KEY: VARIANT
<222> LOCATION: (8)..(8)
<223> OTHER INFORMATION: /replace = "D-Trp"

<400> SEQUENCE: 24

Ala Gly Cys Lys Asn Xaa Phe Xaa Lys Thr Phe Thr Ser Cys
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (7)..(7)
<223> OTHER INFORMATION: /replace = "L-2,4,6-trimethyl-phenylalanine"
<220> FEATURE:
<221> NAME/KEY: VARIANT
<222> LOCATION: (8)..(8)
<223> OTHER INFORMATION: /replace = "D-Trp"

<400> SEQUENCE: 25

Ala Gly Cys Lys Asn Phe Xaa Xaa Lys Thr Phe Thr Ser Cys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)

-continued

```
<220> FEATURE:
<221> NAME/KEY: VARIANT
<222> LOCATION: (8)..(8)
<223> OTHER INFORMATION: /replace = "D-Trp"
<220> FEATURE:
<221> NAME/KEY: VARIANT
<222> LOCATION: (11)..(11)
<223> OTHER INFORMATION: /replace = "L-2,4,6-trymethyl-phenylalanine"

<400> SEQUENCE: 26

Ala Gly Cys Lys Asn Phe Phe Xaa Lys Thr Xaa Thr Ser Cys
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "L-2,4,6-trimethyl-phenylalanine"
<220> FEATURE:
<221> NAME/KEY: VARIANT
<222> LOCATION: (7)..(7)
<223> OTHER INFORMATION: /replace = "L-2,4,6-trimethyl-phenylalanine"

<400> SEQUENCE: 27

Ala Gly Cys Lys Asn Xaa Xaa Trp Lys Thr Phe Thr Ser Cys
 1               5                  10

<210> SEQ ID NO 28
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "L-2,4,6-trimethyl-phenylalanine"
<220> FEATURE:
<221> NAME/KEY: VARIANT
<222> LOCATION: (11)..(11)
<223> OTHER INFORMATION: /replace = "L-2,4,6-trimethyl-phenylalanine"

<400> SEQUENCE: 28

Ala Gly Cys Lys Asn Xaa Phe Trp Lys Thr Xaa Thr Ser Cys
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (7)..(7)
<223> OTHER INFORMATION: /replace = "L-2,4,6-trimethyl-phenylalanine"
<220> FEATURE:
<221> NAME/KEY: VARIANT
<222> LOCATION: (11)..(11)
```

```
<223> OTHER INFORMATION: /replace = "L-2,4,6-trimethyl-phenylalanine"

<400> SEQUENCE: 29

Ala Gly Cys Lys Asn Phe Xaa Trp Lys Thr Xaa Thr Ser Cys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "L-2,4,6-trymethyl-phenylalanine"
<220> FEATURE:
<221> NAME/KEY: VARIANT
<222> LOCATION: (7)..(7)
<223> OTHER INFORMATION: /replace = "L-2,4,6-trymethyl-phenylalanine"
<220> FEATURE:
<221> NAME/KEY: VARIANT
<222> LOCATION: (11)..(11)
<223> OTHER INFORMATION: /replace = "L.-2,4,6-trymethyl-phenylalanine"

<400> SEQUENCE: 30

Ala Gly Cys Lys Asn Xaa Xaa Trp Lys Thr Xaa Thr Ser Cys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Peptide ligand of somatostatin receptor
<220> FEATURE:
<221> NAME/KEY: MISC_FEATURE
<222> LOCATION: (3)..(14)
<223> OTHER INFORMATION: /note: 2-butenylene from Gly in position 3 to
      Gly in position 14

<400> SEQUENCE: 31

Ala Gly Gly Lys Asn Phe Phe Trp Lys Thr Phe Thr Ser Gly
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Peptide ligand of somatostatin receptor
      conjugated to DOTA at the N-terminal residue
<220> FEATURE:
<221> NAME/KEY: DISULFID
<222> LOCATION: (3)..(14)
<220> FEATURE:
<221> NAME/KEY: VARIANT
<222> LOCATION: (6)..(6)
<223> OTHER INFORMATION: /replace = "L-2,4,6-trimethyl-phenylalanine"
<220> FEATURE:
<221> NAME/KEY: VARIANT
<222> LOCATION: (8)..(8)
<223> OTHER INFORMATION: /replace = "D-Trp"

<400> SEQUENCE: 32

Ala Gly Cys Lys Asn Xaa Phe Xaa Lys Thr Phe Thr Ser Cys
1               5                   10
```